US011913952B2

(12) United States Patent
Altin et al.

(10) Patent No.: US 11,913,952 B2
(45) Date of Patent: *Feb. 27, 2024

(54) METHODS FOR DETECTING PEPTIDE/MHC/TCR BINDING

(71) Applicant: Prognosys Biosciences, Inc., San Diego, CA (US)

(72) Inventors: John Andrew Altin, Flagstaff, AZ (US); Mark S. Chee, Encinitas, CA (US)

(73) Assignee: Prognosys Biosciences, Inc., San Diego, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/532,728

(22) Filed: Nov. 22, 2021

(65) Prior Publication Data

US 2022/0146513 A1 May 12, 2022

Related U.S. Application Data

(63) Continuation of application No. 14/776,537, filed as application No. PCT/US2014/029691 on Mar. 14, 2014, now Pat. No. 11,231,419.

(60) Provisional application No. 61/800,891, filed on Mar. 15, 2013.

(51) Int. Cl.
*G01N 33/569* (2006.01)
*C12Q 1/6804* (2018.01)
*G01N 33/538* (2006.01)
*C07K 7/08* (2006.01)

(52) U.S. Cl.
CPC ......... *G01N 33/56977* (2013.01); *C07K 7/08* (2013.01); *C12Q 1/6804* (2013.01); *G01N 33/538* (2013.01); *G01N 2333/003* (2013.01); *G01N 2333/70539* (2013.01)

(58) Field of Classification Search
CPC ................ C07K 7/08; G01N 2333/70539
See application file for complete search history.

(56) References Cited

U.S. PATENT DOCUMENTS

| | | | |
|---|---|---|---|
| 5,002,882 A | 3/1991 | Lunnen et al. |
| 5,512,439 A | 4/1996 | Hornes et al. |
| 6,210,894 B1 | 4/2001 | Brennan |
| 6,258,558 B1 | 7/2001 | Szostak et al. |
| 6,261,804 B1 | 7/2001 | Szostak et al. |
| 6,281,804 B1 | 8/2001 | Haller et al. |
| 6,344,316 B1 | 2/2002 | Lockhart et al. |
| 6,416,950 B1 | 7/2002 | Lohse et al. |
| 6,485,982 B1 | 11/2002 | Charlton |
| 6,518,018 B1 | 2/2003 | Szostak et al. |
| 6,579,695 B1 | 6/2003 | Lambalot et al. |
| 6,632,641 B1 | 10/2003 | Brennan et al. |
| 6,800,453 B2 | 10/2004 | LaBaer et al. |
| 6,878,515 B1 | 4/2005 | Landegren et al. |
| 7,118,883 B2 | 10/2006 | Inoue et al. |
| 7,192,735 B2 | 3/2007 | Lambalot et al. |
| 7,229,769 B2 | 6/2007 | Kozlov et al. |
| 7,270,950 B2 | 9/2007 | Szostak et al. |
| 7,378,242 B2 | 5/2008 | Hurt et al. |
| 7,393,665 B2 | 7/2008 | Brenner |
| 7,407,757 B2 | 8/2008 | Brenner |
| 7,537,897 B2 | 5/2009 | Brenner |
| 7,544,473 B2 | 6/2009 | Brenner |
| 7,579,153 B2 | 8/2009 | Brenner |
| 7,635,566 B2 | 12/2009 | Brenner |
| 7,666,612 B2 | 2/2010 | Johnsson et al. |
| 7,674,752 B2 | 3/2010 | He et al. |
| 7,776,547 B2 | 8/2010 | Roth |
| 7,858,321 B2 | 12/2010 | Glezer et al. |
| 8,207,093 B2 | 6/2012 | Szostak et al. |
| 8,337,851 B2 | 12/2012 | Aukerman |

(Continued)

FOREIGN PATENT DOCUMENTS

| | | |
|---|---|---|
| EP | 1712623 | 10/2006 |
| JP | 2011-182702 | 6/2011 |

(Continued)

OTHER PUBLICATIONS

Advisory Action for U.S. Appl. No. 14/776,537, dated Jul. 13, 2018, 4 pages.
Anderson et al., "Microarrayed Compound Screening to Identify Activators and Inhibitors of AMP-Activated Protein Kinase," J. of Biomolecular Screening (2004) 9:112 POI: 0.1177/1087057103260592.
Angenendt et al., "Cell-free expression and functional assay in a nanowell chip format," Analytical Chemistry (2004) 76(7):1844-49.
Angenendt et al., "Generation of High Density Protein Microarrays by Cell-free in Situ Expression of Unpurified PCR Products," Molecular and Cellular Proteomics, (2006) Ch. 5.9, pp. 1658-1666.
Atkinson, Overview of Translation: Lecture Manuscript, U of Texas (2000) pp. 6.1-6.8.
Blokzijl et al., "Profiling protein expression and interactions: proximity ligation as a tool for personalized medicine," J Intern Med (2010) 268:232-245.

(Continued)

*Primary Examiner* — Sahana S Kaup
(74) *Attorney, Agent, or Firm* — MORRISON & FOERSTER LLP

(57) ABSTRACT

Provided herein are compositions and methods for detecting the binding of a peptide to an MHC molecule, and the binding of a peptide:MHC complex to a TCR. In preferred embodiments, the compositions and methods are in a highly-multiplexed way. The compositions and methods disclosed herein can be used to provide direct information on which peptides are bound to an MHC molecule. Also provided is a method for simultaneously detecting a large number of peptides for binding to an MHC molecule and/or a T cell. A method for detecting competitive binding of a large number of peptides to an MHC molecule and/or a T cell is also disclosed. Also provided herein is a method for simultaneously detecting a large number of specific TCRs. The compositions and methods of the present invention are useful for vaccine design, research and monitoring of autoimmune and infectious disease, immunogenicity testing of therapeutics, and tissue typing.

19 Claims, 9 Drawing Sheets
Specification includes a Sequence Listing.

(56) References Cited

U.S. PATENT DOCUMENTS

| | | |
|---|---|---|
| 8,343,500 B2 | 1/2013 | Wraith |
| 8,394,590 B2 | 3/2013 | Kwong et al. |
| 8,865,414 B2 | 10/2014 | Hennig et al. |
| 9,085,798 B2 | 7/2015 | Chee |
| 11,092,601 B2 | 8/2021 | John et al. |
| 11,231,419 B2 | 1/2022 | Altin et al. |
| 2002/0064779 A1 | 5/2002 | Landegren |
| 2003/0087232 A1 | 5/2003 | Christians et al. |
| 2003/0096323 A1 | 5/2003 | James |
| 2003/0113713 A1 | 6/2003 | Glezer et al. |
| 2003/0232382 A1 | 6/2003 | Brennan et al. |
| 2003/0138879 A1 | 7/2003 | Lambalot et al. |
| 2003/0162216 A1 | 8/2003 | Gold et al. |
| 2003/0224419 A1 | 12/2003 | Corcoran et al. |
| 2003/0235852 A1 | 12/2003 | Roberts et al. |
| 2004/0072246 A1* | 4/2004 | Martin ............ G01N 33/6842 435/7.1 |
| 2004/0112442 A1 | 6/2004 | Maerkl |
| 2005/0003431 A1 | 1/2005 | Wucherpfennig |
| 2005/0026188 A1 | 2/2005 | Van Kessel et al. |
| 2005/0048580 A1 | 3/2005 | LaBaer et al. |
| 2005/0095655 A1 | 5/2005 | Montero-Julian et al. |
| 2005/0164292 A1 | 7/2005 | Faroqui et al. |
| 2005/0255548 A1 | 11/2005 | Lipovsek et al. |
| 2005/0260653 A1 | 11/2005 | LaBaer et al. |
| 2006/0003394 A1 | 1/2006 | Song et al. |
| 2006/0046313 A1 | 3/2006 | Roth et al. |
| 2006/0079453 A1 | 4/2006 | Sideny |
| 2006/0093613 A1* | 5/2006 | Jakobsen ............ A61K 47/6425 536/23.5 |
| 2006/0134669 A1 | 6/2006 | Casasanta, III |
| 2006/0199207 A1 | 9/2006 | Matysiak |
| 2006/0216721 A1 | 9/2006 | Kozlov et al. |
| 2006/0216775 A1 | 9/2006 | Burkhart et al. |
| 2006/0228758 A1 | 10/2006 | Muchhal |
| 2006/0275799 A1 | 12/2006 | Banerjee et al. |
| 2007/0003950 A1* | 1/2007 | Shen ............ C12Q 1/6804 435/6.13 |
| 2007/0014810 A1 | 1/2007 | Baker et al. |
| 2007/0020625 A1 | 1/2007 | Duchaud et al. |
| 2007/0020669 A1 | 1/2007 | Olof |
| 2007/0026430 A1 | 2/2007 | Andersen et al. |
| 2007/0172873 A1 | 7/2007 | Brenner et al. |
| 2008/0071071 A1 | 3/2008 | LaBaer et al. |
| 2008/0108804 A1 | 5/2008 | Hayashizaki et al. |
| 2008/0220981 A1 | 9/2008 | McGregor |
| 2008/0293591 A1 | 11/2008 | Taussig et al. |
| 2008/0312103 A1 | 12/2008 | Nemoto et al. |
| 2009/0280487 A1 | 11/2009 | Hung et al. |
| 2009/0291854 A1 | 11/2009 | Weisinger-Mayr et al. |
| 2010/0168390 A1 | 1/2010 | Brix et al. |
| 2010/0069263 A1 | 3/2010 | Shendure et al. |
| 2010/0099103 A1 | 4/2010 | Hsieh et al. |
| 2010/0113302 A1 | 6/2010 | Williams |
| 2010/0159446 A1 | 6/2010 | Haff |
| 2010/0173384 A1 | 7/2010 | Johnsson et al. |
| 2010/0184614 A1 | 7/2010 | Ye et al. |
| 2011/0245101 A1 | 10/2011 | Chee et al. |
| 2011/0245111 A1 | 10/2011 | Chee |
| 2012/0065081 A1 | 3/2012 | Chee |
| 2012/0129248 A1 | 5/2012 | Chee |
| 2012/0195810 A1 | 8/2012 | Cohen |
| 2012/0258871 A1 | 10/2012 | Kozlov et al. |
| 2012/0270748 A1 | 10/2012 | Chee et al. |
| 2013/0096033 A1 | 4/2013 | Routenberg |
| 2013/0109595 A1 | 5/2013 | Routenberg |
| 2013/0296174 A1 | 11/2013 | Peumans |
| 2015/0087027 A1 | 3/2015 | Makarov |
| 2016/0024576 A1 | 1/2016 | Chee |
| 2016/0025726 A1 | 1/2016 | Altin et al. |
| 2016/0333403 A1 | 11/2016 | Chee |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |
| 2019/0085048 A1 | 3/2019 | Brix et al. |
| 2019/0383813 A1 | 12/2019 | Altin et al. |
| 2022/0146513 A1 | 5/2022 | Atlin et al. |

FOREIGN PATENT DOCUMENTS

| | | | |
|---|---|---|---|
| WO | WO-91/18012 | 11/1991 | |
| WO | WO-9118012 A1 * | 11/1991 | ............ C07K 7/00 |
| WO | WO 2003/010176 | 2/2003 | |
| WO | WO 2004/028955 | 4/2004 | |
| WO | WO 2005/026387 | 3/2005 | |
| WO | WO 2006/117541 | 11/2006 | |
| WO | WO 2007/041689 | 4/2007 | |
| WO | WO 2007/060599 | 5/2007 | |
| WO | WO 2007/073171 | 6/2007 | |
| WO | WO 2007/076726 | 7/2007 | |
| WO | WO 2007/145612 | 12/2007 | |
| WO | WO 2009/032167 | 3/2009 | |
| WO | WO-2009/126828 | 10/2009 | |
| WO | WO 2010/019826 | 2/2010 | |
| WO | WO 2010/027870 | 3/2010 | |
| WO | WO 2010/127186 | 11/2010 | |
| WO | WO 2011/014879 | 2/2011 | |
| WO | WO 2011/071943 | 6/2011 | |
| WO | WO-2011071943 A1 * | 6/2011 | ......... C12N 15/1062 |
| WO | WO 2011/127006 | 10/2011 | |
| WO | WO 2011/127099 | 10/2011 | |
| WO | WO 2012/022975 | 2/2012 | |
| WO | WO 2012/071428 | 5/2012 | |
| WO | WO-2012071428 A2 * | 5/2012 | ............ C07H 21/00 |
| WO | WO 2012/139110 | 10/2012 | |
| WO | WO 2014/145047 | 9/2014 | |
| WO | WO/2014/210223 | 12/2014 | |
| WO | WO/2014/210225 | 12/2014 | |

OTHER PUBLICATIONS

Burns et al., "Well-less, gel-permeation formats for ultra-HTS," DDT (2001) 6(12):S40-S47.

Carlson et al., "Formylglycine-generating Enzyme," J. of Biological Chemistry (2008) 283(29):20117-125.

Cerutti et al., "Generation of sequence-specific, high affinity anti-DNA antibodies," Journal of Biological Chemistry (2001) 276(16):12769-12773.

Cha et al., "Specificity, Efficiency and Fidelity of PCR," Genome Res. (1993) 3:518-29.

Chandra et al., "Cell-free synthesis-based protein microarrays and their applications," Proteomics ePub (2009) 5(6):717-30.

Chatterjee et al., "Protein Microarray On-Demand: A Novel Protein Microarray System," PLos One (2008) 3(9):e3265.

Chen et al., "DNA hybridization detection in a microfluidic Channel using two fluorescently labelled nucleic acid probes", Biosensors and Bioelectronics (2008) 23:1878-1882.

Cheng et al., "Sensitive Detection of Small Molecules by Competitive Immunomagnetic-Proximity Ligation Assay," Anal Chem (2012) 84:2129-2132.

Chou et al., "Short peptide sequences mimic HLA-DM functions," Mol Immuno (2008) 45:1935-1943.

Communication pursuant to Article 94(3) EPC, dated Jun. 14, 2018, 7 pages.

Communication pursuant to Article 94(3) EPC, dated Aug. 18, 2017, 8 pages.

Condina et al., "A sensitive magnetic bead method for the detection and identification of tyrosine phosphorylation in proteins by MALDI-TOF/TOF MS," Proteomics (2009) 9:3047-3057.

Cujec et al. "Selection of v-abl tyrosine kinase substate sequences from randomnized peptide and cellular proteomic libraries using mRNA display," Chemistry and Biology (2002) 9:253-264.

Darmanis, et al., "ProteinSeq: High-Performance Proteomic Analyses by Proximity, Ligation and Next Generation Sequencing", PLos One (2011) 6(9):e25583 doi10.1371/journal .pone.0025583 20 1.

Eisen et al., "Promiscuous binding of extracellular peptides to cell surface class I MHC protein," PNAS (2012) 109(12):4580-4585.

(56) References Cited

OTHER PUBLICATIONS

Eldridge et al. "An in vitro selection strategy for conferring protease resistance to ligand binding peptides," Protein Eng Des Sel (2009) 22(11):691-698.
Ellington et al., "Antibody-based protein multiplex platforms: technical and operational challenges," Clin Chem (2010) 56(2):186-193.
European Search Report for EP 20169866, dated Sep. 25, 2020, 10 pages.
Final Rejection for U.S. Appl. No. 14/776,537, dated Mar. 19, 2018, 17 pages.
Flanigon et al., "Multiplex protein detection with DNA readout via mass spectrometry," N Biotechnol (2013) 30(2):153-158.
Fredriksson et al., "Multiplexed protein detection by proximity ligation for cancer detection," Nature Methods (2007) 4(4):327-29.
Fredriksson et al., "Multiplexed proximity ligation assays to profile putative plasma biomarkers relevant to pancreatic and ovarian cancer," Clin. Chem. (2008) 5(3): 582-89.
Fredriksson et al., "Protein detection using proximity-dependent DNA ligation assays," Nature Biotech. (2002) 20:473-77.
Frese and Dierks, "Formylglycine Aldehyde Tag-Protein Engineering through a Novel Post-translational Modification," ChemBioChem (2009) 10:425-27.
Fu et al., "Counting individual DNA molecules by the stochastic attachment of diverse labels," PNAS (2011) 108:9026-9031.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
He et al. , "In situ synthesis of protein arrays," Current Opinion in Biotechnology (2008) 19:4-9.
He et al., "In situ synthesis of protein arrays," Current Opinion in Biotechnology (2008)19:4-9 Supplementary figures.
He et al., "Printing protein arrays from DNA arrays," Nature Methods (2008) 5:175-77.
He, "Cell-free protein synthesis: applications in proteomics and biotechnology," (2008) New Biotechnology 25:126-132.
Hedskog et al., "Dynamics of HIV-1 Quasispecies during Antiviral Treatment Dissected using Ultra-Deep Pyrosequencing," PLoS One (2010) 5(7)e11345.
Hendrickson et al., "High sensitivity multianalyte immunoassay using covalent DNA-labeled antibodies and polymerase chain reaction," Nucl. Acid Res. (1995) 23(9):522-29.
Hiatt et al., "Parallel, tag-directed assembly of locally-derived short sequence reads," Nature Methods (2010) 7(2):119-25.
Kozlov et al., "A High-Complexity Multiplexed Solution-Phase Assay for Profiling Protease Activity on Microarrays," Comb. Chem. and High Throughput (2008) 11:24-35.
Kozlov et al., "A Highly Scalable Peptide-Based Assay System for Proteomics," PLoS ONE (2012) 7(6):e37441.
Kozlov et al., "A Method for Rapid Protease Substrate Evaluation and Optimization," Comb. Chem. and High Throughput (2006) 9:481-87.
Kurz et al. , "eDNA-Protein Fusions: Covalent Protein-Gene Conjugates for the In Vitro Selection of Peptides and Proteins," ChemBioChem (2001) 2:666-72.
Larman et al., "Autoantigen discovery with a synthetic human peptidome", Nature Biotechnology (2011) doi:1 0.1038/nbt.1856.
Lundberg et al., "Multiplexed homogeneous proximity ligation assays for high-throughput protein biomarker research in serological material," Mol Cell Proteomics (2011) 10(4):M110.004978.
Lundberg et al.,"Homogeneous antibody-based proximity extension assays provide sensitive and specific detection of low-abundant proteins in human blood", Nucleic Acids Res.(2011) 39(15):e1 02 (Abstract).
Mir et al., "Sequencing by cyclic ligation and cleavage (CycLiC) directly on a microarray captured template," Nucleic Acids Research (2009) 37(1):e5-1.

Mizusawa et al., "A bacteriophage lambda vector for cloning with BamHI and Sau3A," Gene (1982) 20:317-322.
Ng et al., "Massively parallel sequencing and rare disease," Human Molec. Genetics (2010) 19(2):R119-R124.
Niemeyer , "The developments of semisynthetic DNA/protein conjugates," Trends Biotechnol (2002) 20(9):395-401.
Non-Final Rejection for U.S. Appl. No. 14/776,537, dated May 2, 2017, 23 pages.
Non-Final Rejection for U.S. Appl. No. 14/776,537, dated May 28, 2019, 20 pages.
Non-Final Rejection for U.S. Appl. No. 14/776,537, dated Oct. 6, 2020, 30 pages.
Oleinikov et al. "Self-assembling protein arrays using electronic semiconductor microchips and in vitro translation," Journal of Proteome Research (2003) 2:313-319.
Osada et al., "Epitope mapping using ribosome display in a resconstituted cell-free protein synthesis system," Journal of Biochemistry, 2009, 145(5):693-700.
O'Shannessy et al., "Detection and Quantitation of Hexa-Histidine-Tagged recombinant proteins on western blots and by a surface plasmon resonance biosensor technique," Analytical Biochemistry (1995) 229:119-124.
Prasad et al., "Effect of chemical chaperones in improving the solubility of recombinant proteins in *Escherichia coli*," Applied and Environmental Microbiology (2011) 4603-4609.
Proseek® Multiplex 96×96 User Manual (2013) Olink Bioscience, Uppsala, Sweden, 20 pages.
Ramachandran et al., "Next-generation high-density self-assembling functional protein arrays," Nature Methods (2008) 5(6):535-38.
Restriction Requirement for U.S. Appl. No. 14/776,537, dated Jan. 6, 2017, 8 pages.
Roberts and Szostak , "RNA-peptide fusions for the in vitro selection of peptides and proteins," PNAS USA(1997) 94:12297-302.
Rouillard et al., "OligoArray 2.0: design of oligonucleotide probes for DNA microarrays using a thermodynamic approach," Nuc. Acid Research (2003) 31 (12):3057-62.
Rountenberg et al., "Microfluidic probe: a new tool for integrating microfluidic environments and electronic wafer-probing," Lab Chip, Oct. 29, 2009, 10: 123-127.
Rush et al., "New Aldehyde Tag Sequences Identified by Screening Formylglycine Generating Enzymes in Vitro and in Vivo," J. of American Chemical Society (2008) 130: 12240-41 (2008) Supplement.
Rush et al., "New Aldehyde Tag Sequences Identified by Screening Formylglycine Generating Enzymes in Vitro and in Vivo," J. of American Chemical Society (2008) 130: 12240-41.
Schmitt et al. , "Detection of ultra-rare mutations by next-generation sequencing," PNAS (2012) 109:14508-14523.
Sergeeva et al., "Display technologies: Application for the discovery of drug and gene delivery agents," Advanced Drug Delivery Reviews (2006) 58(15):1622-1654.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Summons to attend oral proceedings pursuant to Rule 115(1) EPC, dated Feb. 18, 2019, 8 pages.
Takahashi et al., "In Vitro Selection of Protein and Peptide Libraries Using mRNA Display," Nucleic Acid and Peptide Aptamers: Methods and Protocols (2009) 535:293-314 (Ch.17).
Tian et al., "Antigen peptide-based immunosensors for rapid detection of antibodies and antigens," Anal Chem (2009) 81:5218-5225.
Tolbert et al., "New Methods for Proteomic Research: Preparation of Proteins with N-Terminal Cysteines for Labeling and Conjugation," Angew. Chem. Int. Ed. (2002) 41(12):2171-74.
Valencia et al., "mRNA-display-based selections for proteins with desired functions: A protease-substrate case study," Biotechnology Progress, 2008, 24(3): 561-569.
Vogelstein et al., "Digital PCR," PNAS USA (1999) 96:9236-41.

(56) References Cited

OTHER PUBLICATIONS

Waichman et al., "Functional Immobilization and Patterning of Proteins by an Enzymatic Transfer Reaction", Anal. Chem. (2010) 82:1478-85.
Weichhart et al., "Functional selection of vaccine candidate peptides from *Staphylococcus aureus* whole-genome expression libraries in vitro," Infection and Immunity, 2003, 71(8):4333-4641.
Wong et al. "Direct Site-Selective Covalent Protein Immobilization Catalyzed by a Phosphopantetheinyl Transferase," J. Am. Chem Soc. (2008) 130:12456-64.
Worthington et al., "Cloning of random oligonucleotides to create single-insert plasmid libraries," Analyt. Biochem (2001) 294:169-175.
Xiao et al., "Direct determination of haplotypes from single DNA molecules," Nature Methods(2009) 6(3):199-01.
Yin et al., "Genetically encoded short peptide tag for versatile protein labeling by Sfp phosphopantetheinyl transferase," PNAS (2005) 102(44):15815-20.
Yonezawa et al., "DNA display for in vitro selection of diverse peptide libraries", Nucleic Acids Research (2003) 31(19):e118.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Zhou et al., "Genetically Encoded Short Peptide Tags for Orthogonal Protein Labeling by Sfp and AcpS Phosphopentetheinyl Transferases," ACS Chemical Biology (2007) 2(5):337-346.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.
Sewell et al., "Why must T cells be cross-reactive?" Nature Reviews Immunology (2012) 12:669-677.

* cited by examiner

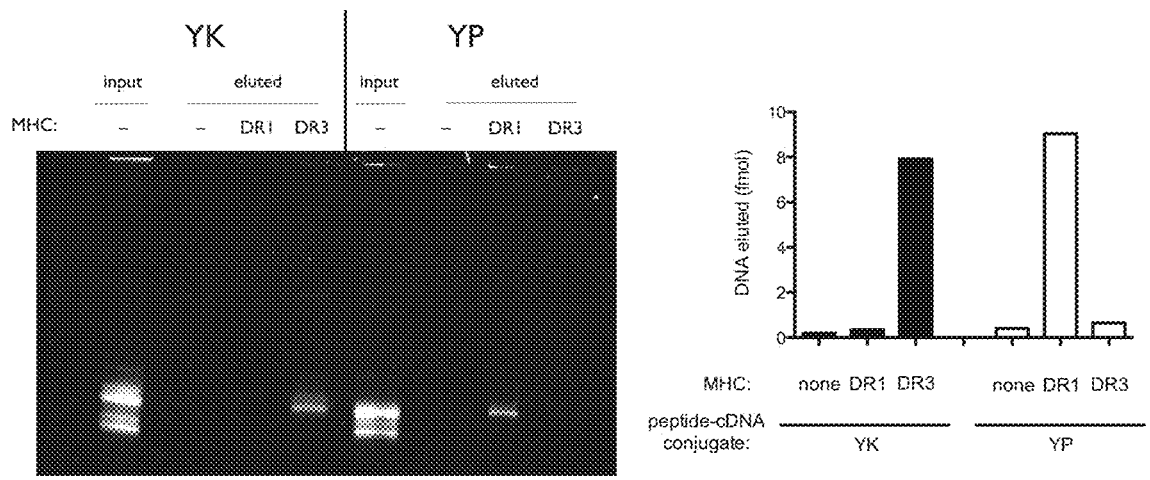
FIG. 4A  FIG. 4B
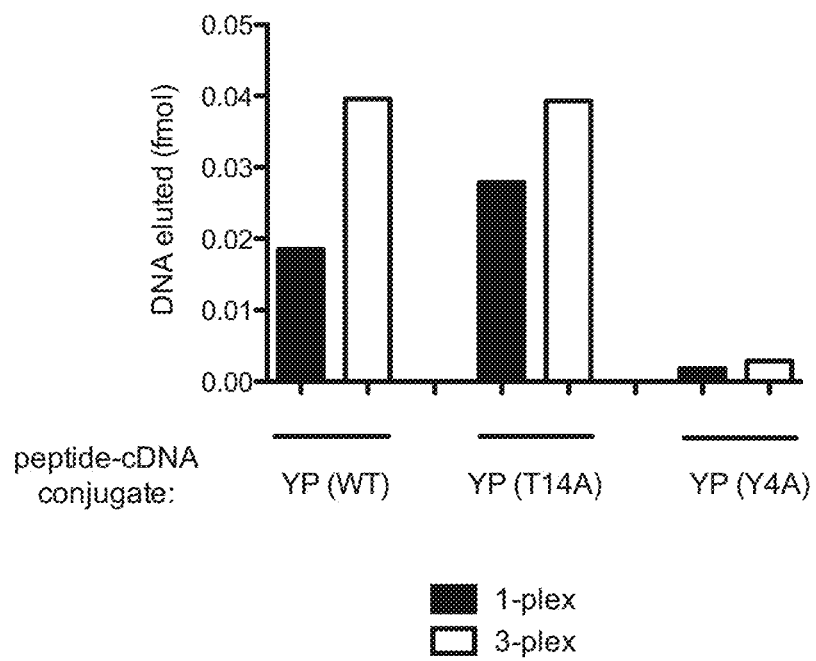
FIG. 5

METHODS FOR DETECTING PEPTIDE/MHC/TCR BINDING

RELATED APPLICATIONS

This application is a continuation of U.S. Ser. No. 14/776,537, which is a U.S. National Stage Application of International Application No. PCT/US2014/029691, filed Mar. 14, 2014, which claims priority to U.S. Provisional Patent Application Ser. No. 61/800,891, filed on Mar. 15, 2013. The contents of the above-identified applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699932000102SeqList.txt, date recorded: Nov. 6, 2021, size: 1.98 KB).

TECHNICAL FIELD

The present invention is in the field of immunology, and relates to protein interactions in the immune system. Specifically, the present invention relates to peptide-MHC interactions and methods and compositions for detecting the interactions.

BACKGROUND

Immunology is fundamentally concerned with the interaction between a host, an organism whose immune system mounts a response; and an immunogen, the agent against which that response is directed. The outcome of this interaction dictates the host's fate: for a pathogenic immunogen, infection; for an altered-self immunogen, cancer; for a self immunogen, autoimmunity; and for an innocuous environmental immunogen, allergy. Improvements in DNA sequencing capacity have provided tools to explore the genetic basis of these different immune outcomes at high-resolution and with broad-coverage, with reference to both host and immunogen genomes (Peng et al., 2009, Curr. Opin. Microbiol. 12: 432-438; Benichou et al., 2012, Immunology 135: 183-191).

One of the most important protein interface between the host and immunogen is the peptide:major histocompatibility (p:MHC) complex, which comprises a host-encoded transmembrane protein (MHC) in physical association with an immunogen-derived peptide. This complex serves two parallel systems of antigen presentation: (1) the cytosolic pathway, in which endogenous proteins are processed into short peptides, e.g., peptides of approximately 7-10 amino acids, and presented in complex with MHC class I by all nucleated cells; and (2) the endosomal pathway, in which engulfed exogenous proteins are processed into peptides of approximately 10-25 amino acids and presented in complex with MHC class II by specialized antigen presenting cells (Germain, 1994, Cell 76: 287-299). Once presented to the adaptive immune system in one of these ways, immunogen-derived peptides can trigger a highly antigen-specific response, for example, a cellular immune response versus a humoral immune response, or an immunogenic response versus a tolerogenic response.

SUMMARY OF THE INVENTION

Compositions and methods for detecting peptide/MHC binding are disclosed. Provided herein is an MHC-binding peptide conjugated to a polynucleotide. In certain embodiments, the polynucleotide can be DNA, cDNA, RNA, mRNA, rRNA, tRNA, PNA, a DNA-like molecule or an RNA-like molecule.

Also provided is a library of at least two MHC-binding peptides each conjugated to a polynucleotide, wherein each said polynucleotide is identified by a probe that specifically binds to said polynucleotide. In certain embodiments, the polynucleotide and the probe can be DNA, cDNA, RNA, mRNA, rRNA, tRNA, PNA, a DNA-like molecule or an RNA-like molecule.

Provided herein is a composition comprising at least two MHC-binding peptides each conjugated to a polynucleotide, wherein the at least two MHC-binding peptides are multimerized or oligomerized. In one aspect, the at least two MHC-binding peptides are conjugated to the same polynucleotide and are thus multimerized or oligomerized. In other embodiments, the at least two MHC-binding peptides are each conjugated to a separate polynucleotide, wherein the polynucleotides mediate the multimerization or oligomerization of the at least two MHC-binding peptides. In some embodiments, the multimerization or oligomerization is mediation by nucleotide sequence complementarity.

In one embodiment, a method for detecting binding of a peptide to an MHC molecule is disclosed. The method comprises: contacting said MHC molecule with a polynucleotide-peptide conjugate, said polynucleotide-peptide conjugate comprising said peptide and a polynucleotide; contacting said polynucleotide-peptide conjugate with a probe that specifically binds to said polynucleotide; detecting binding of said probe to said polynucleotide; and, correlating binding of said probe to said polynucleotide with binding of said peptide to said MHC molecule.

In another embodiment, a method for simultaneously detecting binding of a library of peptides to an MHC molecule is provided. The method comprises: providing a polynucleotide-peptide conjugate for each said peptide, said polynucleotide-peptide conjugate comprising said peptide and a polynucleotide; contacting said MHC molecule with a pool of said polynucleotide-peptide conjugates; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said MHC molecule. In another embodiment, the method further comprises comparing binding, for example, in terms of binding specificity and/or binding affinity, of each said peptide to said MHC molecule, among the peptides in said library.

In yet another embodiment, provided herein is a method for detecting in a library of peptides competitive binding of each said peptide to an MHC molecule, comprising: providing a polynucleotide-peptide conjugate for each said peptide, said polynucleotide-peptide conjugate comprising said peptide and a polynucleotide; contacting said MHC molecule with a pool of said polynucleotide-peptide conjugates; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said MHC molecule, wherein said peptides compete for binding of said MHC molecule. In another embodiment, the method further comprises comparing binding, for example, in terms of binding specificity and/or binding affinity, of each said peptide to said MHC molecule, among the peptides in said library.

In one aspect, disclosed herein is a method for detecting binding of a peptide to a T cell, comprising: contacting said T cell with an MHC molecule and a polynucleotide-peptide conjugate, said polynucleotide-peptide conjugate comprising said peptide and a polynucleotide; contacting said polynucleotide-peptide conjugate with a probe that specifically binds to said polynucleotide; detecting binding of said probe to said polynucleotide; and, correlating binding of said probe to said polynucleotide with binding of said peptide to said T cell.

In another aspect, a method for simultaneously detecting binding of a library of peptides to a T cell is provided. This method comprises: providing a polynucleotide-peptide conjugate for each said peptide, said polynucleotide-peptide conjugate comprising said peptide and a polynucleotide; contacting said T cell with a pool of said polynucleotide-peptide conjugates and an MHC molecule; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said T cell. In one embodiment, the peptide of the present invention binds a TCR of said T cell.

In yet another aspect, described herein is a method for detecting in a library of peptides competitive binding of each said peptide to a T cell, comprising: providing a polynucleotide-peptide conjugate for each said peptide, said polynucleotide-peptide conjugate comprising said peptide and a polynucleotide; contacting said T cell with a pool of said polynucleotide-peptide conjugates and an MHC molecule; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said T cell, wherein said peptides compete for binding of said MHC molecule and said T cell. In one embodiment, the peptide binds a TCR of said T cell.

In any of the embodiments or any combination thereof, the TCR can be a TCR on a T cell, a soluble TCR, an isolated TCR, and an immobilized TCR. Any functional fragment or portion of a TCR is also encompassed by the present invention.

In any of the embodiments or any combination thereof, the method of the present invention can further comprise comparing the detected binding of said peptide to said MHC molecule, said T cell, or said TCR with a reference. In a further embodiment, the method of the present invention as disclosed in any of the embodiments or any combination thereof further comprises selecting the detected binding of said peptide over a reference, for the purposes of identifying antigens in infection, autoimmunity, allergy, or cancer, or for vaccine design.

In any of the embodiments or any combination thereof, the polynucleotide and the probe are selected from the group consisting of DNA, cDNA, RNA, mRNA, rRNA, tRNA, PNA, a DNA-like molecule or an RNA-like molecule. In any of the embodiments or any combination thereof, the binding of said probe to said polynucleotide can be detected by gel electrophoresis, hybridization, PCR, qPCR, or nucleotide sequencing.

In the method of the present invention as disclosed in any of the embodiments or any combination thereof, the MHC molecule can be immobilized. In another embodiment, said polynucleotide-peptide conjugate is multimerized or oligomerized in the method of the present invention as disclosed in any of the embodiments or any combination thereof. In yet another embodiment, the method of the present invention is performed in a high throughput fashion.

In any of the embodiments disclosed herein, a method of the present disclosure further comprises one or more of the steps of: allowing binding between the polynucleotide-peptide conjugate and the MHC molecule to reach equilibrium; washing the complex formed between the polynucleotide-peptide conjugate and the MHC molecule under a suitable condition to remove unbound or non-specifically bound polynucleotide-peptide conjugate; allowing the complex between the polynucleotide-peptide conjugate and the MHC molecule to dissociate, for example, for a suitable period of time; and detecting the polynucleotide-peptide conjugate that remains bound to the MHC molecule.

In any of the preceding embodiments, the complex between the polynucleotide-peptide conjugate and the MHC molecule can be allowed to dissociate in the presence of one or more blocker species. In one aspect, the one or more blocker species prevent binding or reassociation of the polynucleotide-peptide conjugate to the MHC molecule. In some embodiments, the blocker species compete with the polynucleotide-peptide conjugate for binding to the MHC molecule. In one aspect, the binding between the blocker species and the MHC complex does not generate a signal indicative of specific binding between the polynucleotide-peptide conjugate and the MHC molecule.

In any of the embodiments disclosed herein, the binding of the polynucleotide-peptide conjugate to the MHC molecule can occur in the presence of one or more chaperons. In some embodiments, the chaperon is selected from the group consisting of a protein chaperon, a chemical chaperon, HLA-DM and an analogue thereof, a small molecule that has the same or similar chaperon function as HLA-DM, parachlorophenol (pCP) and an analogue thereof, and dimethylsulphoxide (DMSO) and an analogue thereof.

BRIEF DESCRIPTION OF THE DRAWINGS

FIG. 1 (lower panel) shows a multiplexed assay for T cell specificity detection. MHC molecules are incubated with multivalent peptide-cDNA conjugates and a biological sample containing T cells. T cell bound peptide cDNA:MHC complexes are then isolated and detected by high throughput sequencing.

FIGS. 4A-4B show sequence-specific binding of peptide-cDNA conjugates to MHC molecules. Peptide-cDNA conjugates with the sequences YKTIAFDEEARR ("YK") (SEQ ID NO: 1) or YPKYVKQNTLKLAT ("YP") (SEQ ID NO: 2) were incubated either alone ("none"), or in the presence of biotinylated HLA-DR1 ("DR1") or HLA-DR3 ("DR3") MHC molecules. Following incubation, binding complexes were captured on streptavidin beads, washed, and eluted. Eluted DNA was imaged by gel electrophoresis (FIG. 4A), and quantified by qPCR (FIG. 4B). The peptides YKTIAFDEEARR (SEQ ID NO: 1) and YPKYVKQNTLKLAT (SEQ ID NO: 2) are known to bind the DR3 and DR1 molecules, respectively.

FIG. 5 shows multiplex binding of peptide-cDNA conjugates to an MHC molecules. Peptide-cDNA conjugates with the sequences YPKYVKQNTLKLAT ("YP (WT)") (SEQ ID NO: 3), YPKYVKQNTLKLAA ("YP (T14A)") (SEQ ID NO: 4), and YPKAVKQNTLKLAT ("YP (Y4A)") (SEQ ID NO: 5) were produced by in vitro transcription and translation from DNA templates. The three peptide-cDNA conjugates were then incubated, either individually ("1-plex") or mixed in equal ratios ("3-plex"), together with biotinylated HLA-DR1 ("DR1") MHC molecules. Following incubation, binding complexes were captured on streptavidin beads, washed, and eluted. Eluted DNA was quantified by qPCR. The peptides YPKYVKQNTLKLAT (SEQ ID NO: 3), YPKYVKQNTLKLAA (SEQ ID NO: 4) and YPKAVKQNTLKLAT (SEQ ID NO: 5) are known to bind the DR1 molecule with high, high and low affinities, respectively.

DETAILED DESCRIPTION

A. Definitions

Figure 1:
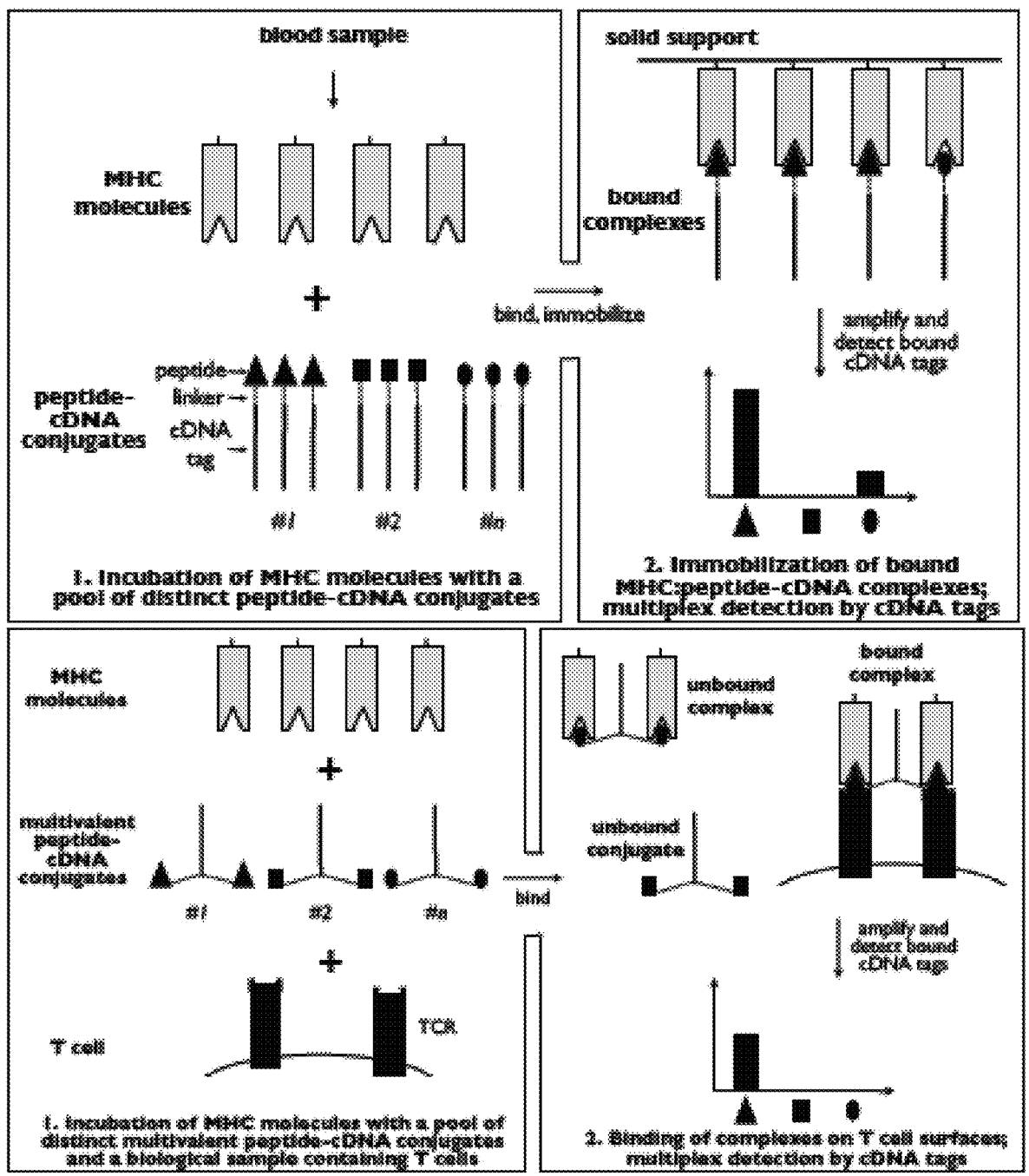
FIG. 1 (upper panel) shows a multiplexed peptide-MHC binding assay. MHC molecules are tested in a pooled binding reaction against a set of in silico-programmed peptide-cDNA conjugates. Bound peptides are identified by high throughput DNA sequencing, which has the dynamic range to reveal the spectrum of differentially-competitive MHC binders (illustrated here in the order triangle>circle>square).

Unless defined otherwise, all terms of art, notations and other technical and scientific terms or terminology used herein are intended to have the same meaning as is commonly understood by one of ordinary skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application and the bibliography and attachments are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims. In the following description of certain embodiments provided here, reference is made to the accompanying drawings which form a part hereof, and in which is it shown by way of illustration specific embodiments in which the invention can be practiced. It is to be understood that other embodiments can be used and structural changes can be made without departing from the scope of the invention.

The practice of the provided embodiments will employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W. B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "a" or "an" means "at least one" or "one or more."

"Individual" means any living organism, including humans and other mammals.

By "subject" is meant an organism to which the provided compositions, methods, kits, and devices can be administered or applied. In one embodiment, the subject is a mammal or a cell, a tissue, an organ or a part of the mammal. Mammals include, but are not limited to, humans, and non-human animals, including farm animals, sport animals, rodents and pets.

As used herein, a "composition" refers to any mixture of two or more products or compounds. It may be a solution, a suspension, liquid, powder, a paste, aqueous, non-aqueous or any combination thereof.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

The terms "nucleic acid" and "nucleic acid sequence" refer to oligonucleotides, nucleotides, polynucleotides, and fragments of any of these, including DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin. The term encompasses nucleic acids, i.e., oligonucleotides, containing known analogues of natural nucleotides, naturally occurring nucleic acids, synthetic nucleic acids, and recombinant nucleic acids.

"Recombinant," as applied to a polynucleotide, means that the polynucleotide is the product of various combinations of cloning, restriction and/or ligation steps, and other procedures that result in a construct that is distinct from a polynucleotide found in nature.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance.

Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities.

As used herein, "production by recombinant means" refers to production methods that use recombinant nucleic acid methods that rely on well-known methods of molecular biology for expressing proteins encoded by cloned nucleic acids.

As used herein, "substantially identical" to a product means sufficiently similar so that the property of interest is sufficiently unchanged so that the substantially identical product can be used in place of the product.

As used herein, "equivalent," when referring to two sequences of nucleic acids means that the two sequences in question encode the same sequence of amino acids or equivalent proteins. It also encompasses those that hybridize under conditions of moderate, preferably high stringency, whereby the encoded protein retains desired properties.

As used herein, when "equivalent" is used in referring to two proteins or peptides, it means that the two proteins or peptides have substantially the same amino acid sequence with only conservative amino acid substitutions that do not substantially alter one or more activities or functions of the protein or peptide. When "equivalent" refers to a property, the property does not need to be present to the same extent (e.g., two peptides can exhibit different rates of the same type of enzymatic activity), but the activities are preferably substantially the same. "Complementary," when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

The terms "polypeptide," "peptide," and "protein" are used interchangeably to refer to polymers of amino acids of any length. These terms also include proteins that are post-translationally modified through reactions that include glycosylation, acetylation and phosphorylation.

As used herein, a "fragment thereof" "region thereof" and "portion thereof" refer to fragments, regions and portions that substantially retain at least one function of the full length polypeptide.

The terms "mimetic", "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif, including, but not limited to, an MHC molecule or a portion or region thereof that specifically binds to a peptide).

Peptide mimetics include recombinantly and chemically modified peptides, and non-peptide agents. Knowing the binding and structural features of the provided peptide:MHC complexes and proteins thereof, one of skill in the art can design peptidomimetics having equivalent, or substantially equivalent, structure and/or function, such as, for example, the same, about the same, greater, or lower binding affinity, compared to a given molecule or complex. The mimetics include those entirely composed of synthetic, non-natural analogues of amino acids, and chimeric molecules composed of natural peptide amino acids and non-natural analogs of amino acids. The mimetics further include polypeptide incorporating conservative amino acid substitutions, as long as such substitutions also do not substantially alter the mimetic's structure and/or activity.

The polypeptides and peptides provided herein, and polypeptides and peptides used in the provided complexes, compositions, combinations and methods, can contain "mimetic" ("peptidomimetic") forms.

As used herein, a variant of a polypeptide (protein) or polynucleotide (namely a parent polypeptide or polynucleotide) is a protein or polynucleotide that contains one or more alterations in the amino acid or nucleic acid sequence, respectively, compared to the amino acid sequence of the parent polypeptide or the nucleic acid sequence of the parent polynucleotide. Alterations in sequences include substitutions, including conservative substitutions, deletions, additions and insertions, compared to the sequence of the polypeptide or polynucleotide of interest. A "conservative" amino acid substitution is a substitution of an amino acid having similar structural or chemical property compared to the corresponding amino acid in the parent polypeptide. Non-conservative amino acid substitutions are those where the charge, hydrophobicity and/or bulk of the amino acid is substantially altered. Typically, a variant polypeptide has at least 75% sequence identity, and preferably at least 80%, 85%, 90%, 95%, or 95% sequence identity sequence identity, to the basic sequence. There may be at least 80%, for example at least 85%, 90% or 95%, amino acid identity over a stretch of 40 or more, for example 60, 80, 100 or more, contiguous amino acids ("hard homology").

Variants of polypeptides may be generated by conventional techniques, including either random or site-directed mutagenesis of DNA encoding the polypeptide. The resultant DNA fragments are then cloned into suitable expression hosts such as *E. coli* or mammalian cells using conventional technology and clones that retain the desired activity are detected. The term "variant" also includes naturally occurring allelic variants.

"Derivative" refers to a polypeptide or polynucleotide that has been derived from a parent polynucleotide or polypeptide the basic sequence by modification, for example by conjugation or complexing with other chemical or protein moieties or by post-translational modification techniques as would be understood in the art. Such derivatives include amino acid deletions and/or additions to polypeptides or variants thereof wherein said derivatives retain activity of the basic protein.

Other derivatives include modification to side chains, incorporation of unnatural amino acids and/or their derivatives during peptide, polypeptide or protein synthesis and the use of crosslinking agents.

B. MHC, MHC Binding Peptides, and Their Implications for Diseases i. MHC

As used herein, the term "Major Histocompatibility Complex" and the abbreviation "MHC" means the complex of genes, found in all vertebrates, which function in signaling between lymphocytes and antigen presenting cells in normal immune responses by binding peptides and presenting them for possible recognition by T cell receptors (TCRs). In a natural setting within the cell, MHC molecules may bind peptides in an intracellular processing compartment and present these peptides on the surface of antigen presenting cells to T cells.

MHC proteins are generally classified into two categories: class I and class II MHC proteins. As used herein, the term "MHC class I" or "class I" refers to Major Histocompatibility Complex class I proteins, binding peptides, or genes, and the term "MHC class II" or "class II" refers to Major Histocompatibility Complex class II proteins, binding peptides, or genes. The human MHC region, also referred to as HLA, is found on chromosome six and includes the class I gene region and the class II gene region. The MHC class I gene region includes the class I α genes HLA-A, HLA-B and HLA-C. The MHC class II region includes the DP, DQ and DR subregions for Class II α chain and β chain genes (i.e., DPα, DPβ, DQα, DQβ, DRα, and DRβ).

An MHC class I protein is an integral membrane protein comprising a glycoprotein heavy chain (α chain), which has three extracellular domains (i.e., α1, α2 and α3), a transmembrane domain, and a cytoplasmic domain. An MHC class I α chain (or class I heavy chain) can be any naturally occurring polypeptide, or one encoded by an artificially mutated α chain gene, essentially corresponding to at least the α1 and α2 domains of one of the gene products of an MHC class I α gene (e.g. HLA-A, HLA-B or HLA-C gene). The transmembrane and cytoplasmic domains may be omitted while an MHC class I α chain retains biological activity. An MHC class I α chain can be any variant with and without the usual glycosylation of the α2 domain, or any allelic variant of a class I α gene, as well as any equivalents, including those which may be produced synthetically or recombinantly by, for example, site-directed mutagenesis of a naturally occurring variant. An MHC class I molecule can be a covalently or non-covalently joined complex of an MHC class I α chain and a soluble subunit called the $β_2$-microglobulin chain (also known as the class I light chain, or the class IP chain). A class I β chain can be any naturally occurring polypeptide, or one encoded by an artificially mutated $β_2$-microglobulin gene, essentially corresponding to the gene product of a $\beta_2$-microglobulin gene. A class I $\beta$ chain can be any allelic variants of $\beta_2$-microglobulin, as well as any equivalents, including those which may be produced synthetically of recombinantly by, for example, site-directed mutagenesis of a naturally occurring variant.

An MHC class II protein is a heterodimeric integral membrane protein comprising one $\alpha$ chain and one $\beta$ chain. The $\alpha$ chain has two extracellular domains (i.e., $\alpha$1 and $\alpha$2), a transmembrane domain, and a cytoplasmic domain. The $\beta$ chain contains two extracellular domains (i.e., $\beta$1 and $\beta$2), a transmembrane domain, and a cytoplasmic domain. An MHC class II $\alpha$ chain (or class II heavy chain) can be any naturally occurring polypeptide, or one encoded by an artificially mutated a gene, essentially corresponding to at least the $\alpha$1 and $\alpha$2 extracellular domains of one of the gene products of an MHC class II $\alpha$ gene. The transmembrane and cytoplasmic domains may be omitted while an MHC class II $\alpha$ chain retains biological activity. An MHC class II $\alpha$ chain can be any variant with and without the usual glycosylation of the $\alpha$1 and $\alpha$2 domains, or any allelic variant of a class II $\alpha$ gene, as well as any equivalents, including those which may be produced synthetically or recombinantly by, for example, site-directed mutagenesis of a naturally occurring variant. An MHC class II molecule can be a covalently or non-covalently joined complex of an MHC class II $\alpha$ chain and an MHC class II $\beta$ chain (also known as the class II light chain, or the class II $\beta$ chain). A class II $\beta$ chain can be any naturally occurring polypeptide, or one encoded by an artificially mutated class II $\beta$ gene, essentially corresponding to at least the $\beta$1 and $\beta$2 extracellular domain of one of the gene products of an MHC class II $\beta$ gene. The transmembrane and cytoplasmic domains may be omitted while an MHC class II $\beta$ chain retains biological activity. An MHC class II $\beta$ chain can be any variant with and without the usual glycosylation of the $\beta$1 domain, or any allelic variant of a class II $\beta$ gene, as well as any equivalents, including those which may be produced synthetically or recombinantly by, for example, site-directed mutagenesis of a naturally occurring variant.

Many mammalian MHC molecules, including human MHC molecules are well known in the art. Without being bound by any theory, any MHC class I or class II molecules can be used in the present invention.

The terms "MHC-peptide complex," "MHC-peptide molecule," "peptide-MHC complex," and "peptide-MHC molecule" are used interchangeably. Any portion of an MHC protein that forms a functional peptide binding groove and that has a peptide bound to the peptide binding groove can be the peptide-MHC complex of the present invention. The terms "binding site," "binding groove" and "binding domain" of an MHC molecule are used interchangeably unless specified otherwise. It is well known in the art that the domain organization of class I and class II molecules forms the antigen binding site, or peptide binding groove. A peptide binding groove refers to a portion of an MHC protein that forms a cavity in which a peptide can bind. According to the present invention, "a portion" of an MHC chain refers to any portion of an MHC chain that is sufficient to form a peptide binding groove upon association with a sufficient portion of another chain of an MHC protein. The conformation of a peptide binding groove is capable of being altered upon binding of an antigenic peptide to enable proper alignment of amino acid residues important for T cell receptor (TCR) binding to the MHC protein and/or peptide.

An MHC class I binding domain (or groove) is formed primarily by the $\alpha$1 and $\alpha$2 domains of an MHC class I $\alpha$ chain. In a preferred embodiment, an MHC class I binding domain includes the $\alpha$3 domain of an $\alpha$ chain and $\beta_2$-microglobulin, which may function to stabilize the over-all structure of the MHC class I molecule. An MHC class I binding domain may also be essentially defined as the extracellular domain of an MHC class I molecule. In certain aspects, a portion of the extracellular domain may be omitted while retaining biological activity. For most MHC class I molecules, interaction of the $\alpha$ and $\beta$ chains can occur in the absence of a peptide. However, the two chain complex of MHC class I is inherently unstable until the binding groove is filled with a peptide.

A peptide binding groove of a class II protein can comprise portions of the $\alpha$1 and $\beta$1 domains. In one embodiment, an MHC class II binding domain minimally includes the $\alpha$1 and $\beta$1 domains. In a preferred embodiment, an MHC class II binding domain includes the $\alpha$2 and $\beta$2 domains, which are believed to stabilize the over-all structure of the MHC binding cleft. An MHC class II binding domain may also be essentially defined as the extracellular domain of an MHC class II molecule. In certain aspects, a portion of the extracellular domain may be omitted while retaining biological activity.

In certain aspects, provided herein is a soluble MHC protein comprising any portions of MHC chains suitable to form a peptide binding groove, including any suitable portion of the extracellular domains of an MHC chain. A soluble MHC protein lacks amino acid sequences capable of anchoring the molecule into a lipid-containing substrate, such as an MHC transmembrane domain and/or an MHC cytoplasmic domain.

ii. MHC Binding Peptides, and MHC Binding Peptide Libraries/Pools

An MHC-binding peptide (e.g., an antigenic peptide or T cell epitope) of the present invention can comprise any peptide that is capable of binding to an MHC protein. In preferred embodiments, the peptide binds to an MHC protein in a manner such that the peptide-MHC complex can bind to a TCR. In further preferred embodiments, the peptide-MHC complex, upon binding to a TCR, induces a T cell response. The MHC binding peptide of the present invention can be an MHC class I binding peptide and/or an MHC class II binding peptide. An MHC class I binding peptide can be a polypeptide which is capable of selectively binding within the binding cleft formed by a specified MHC class I molecule to form a class I MHC-peptide complex. An MHC class I binding peptide is typically 8-10 amino acid residues in length, and may be longer or shorter and still effective. An MHC class II binding peptide can be a polypeptide which is capable of selectively binding within the binding cleft formed by the $\alpha$ and $\beta$ chains of a specified MHC class II molecule to form a class II MHC-peptide complex. An MHC class II binding peptide is typically 10-25, and more typically 13-18, amino acid residues in length, and may be longer or shorter and still effective. In certain embodiments, an MHC-binding peptide (including an MHC class I binding peptide and an MHC class II binding peptide) may be a self or non-self peptide, or a synthetic peptide. In certain aspects, an MHC binding peptide can be processed, for example, by an antigen presenting cell (APC). In other aspects, an MHC binding peptide is not processed by a cell before contacting an MHC molecule of the present invention.

Provided herein are candidate MHC-binding peptides, each produced to be a candidate for binding to an MHC molecule and/or binding to a TCR. As such, a "candidate MHC-binding peptide," a "candidate antigenic peptide" and an "MHC-binding peptide" can be used interchangeably. An MHC-binding peptide that binds to an MHC molecule and is recognized, in conjunction with the MHC molecule, by a TCR, is considered to be an antigenic peptide.

In cells, class I MHC proteins typically present antigenic peptides derived from proteins actively synthesized in the cytoplasm of the cell. In contrast, class II MHC proteins typically present antigenic peptides derived either from exogenous proteins that enter a cell's endocytic pathway or from proteins synthesized in the ER. Intracellular trafficking permits an antigenic peptide to become associated with an MHC protein. The resulting MHC-peptide complex then travels to the surface of the cell where it is available for interaction with a TCR. Candidate MHC-binding peptides of the present invention, however, can be generated or obtained by any suitable methods known to one of skill in the art. In certain embodiments, the candidate MHC-binding peptides can be peptides produced by hydrolysis. In other embodiments, the candidate MHC-binding peptides are synthetically produced peptides, including randomly generated peptides, specifically designed peptides, and peptides where at least some of the amino acid positions are conserved among several peptides and the remaining positions are random.

The binding of a peptide to an MHC peptide binding groove can control the spatial arrangement of MHC and/or peptide amino acid residues recognized by a TCR. Upon identification of MHC binding peptides using methods of the present invention, how peptides bind to the MHC molecule can be determined. For example, the major MHC anchor amino acids of a peptide which are typically held constant can be determined. In another aspect, the surface exposed amino acids that are varied among different peptides can be determined. In one embodiment, the length of an MHC-binding peptide is from about 5 to about 40 amino acid residues, preferably from about 6 to about 30 amino acid residues, and more preferably from about 8 to about 20 amino acid residues, and even more preferably between about 9 and 11 amino acid residues, including any size peptide between 5 and 40 amino acids in length, in whole integer increments (i.e., 5, 6, 7, 8, 9 . . . 40). While naturally MHC class II-bound peptides vary from about 9-40 amino acids, in nearly all cases the peptide can be truncated to an about 9-11 amino acid core without loss of MHC binding activity or T cell recognition. Without being bound by any theory, the MHC binding peptides of the present invention encompass peptides disclosed in any embodiments of the present invention or any combination thereof.

Peptides used in the invention can include peptides comprising at least a portion of an antigen selected from a group consisting of autoantigens, infectious agents, toxins, allergens, or mixtures thereof. However, one aspect of the invention is the use of synthetically produced peptides to identify the peptides bound to a particular MHC at a spectrum of specificities and/or affinities, and to identify the antigens recognized by a specific T cell at a spectrum of specificities and/or affinities. Therefore, preferred peptides are from libraries of synthetically produced peptides, including, but not limited to, peptide libraries produced by PCR (including by introducing random mutations into various positions of a template peptide). A peptide library (used herein interchangeably with "peptide pool") can include at least 2, and up to about 5, about 10, about 20, about 30, about 40, about 50, about 60, about 70, about 80, and about 90 member peptides. In other embodiments, a peptide library includes up to about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, and about $1\times10^4$ member peptides. Without being bound by any theory, a peptide library of the present invention can include up to about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, or about $1\times10^5$ member peptides. In certain embodiments, a peptide library of the present can include more than about $1\times10^5$ member peptides. In some cases, T cell recognition is dominated by only a few amino acids in the core of the peptide, and in these cases, libraries with only a few hundred to a few thousand members are sufficient to identify functional peptide-MHC complexes.

Figure 2:
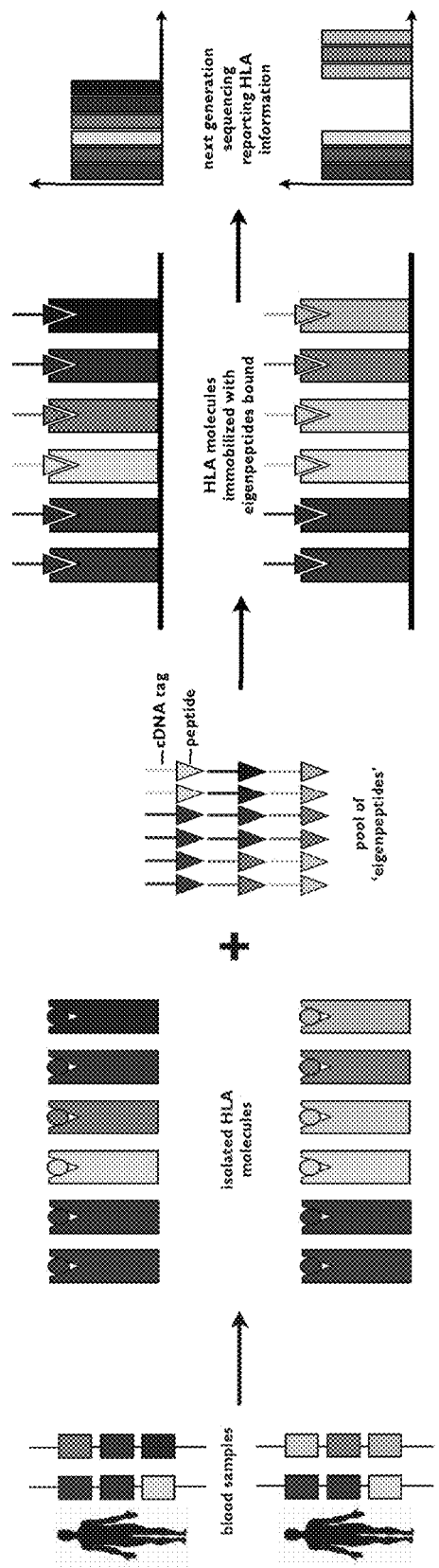
FIG. 2 shows the use of the multiplexed peptide-MHC binding assay with pooled "eigenpeptides" to report individuals' HLA information. HLA molecules are isolated from the blood of donors with different HLA genotypes and tested against a complex pool of peptide-cDNA conjugates. This pool is designed with the aid of the IEDB to cover all listed human haplotypes, with an emphasis on peptides that bind HLA molecules as uniquely as possible ("eigenpeptides"). Next generation sequencing of bound peptide-cDNA conjugates provides information about the HLA molecules that are present. In this example, the two depicted individuals share 1 out of their 2 HLA haplotypes.

Extensive knowledge regarding the binding of peptides to MHC complexes is available to the public, so that for a given MHC complex, one can design MHC-groove binding peptides that vary in less than all of the available positions. For example, the MHCBN is a comprehensive database of Major Histocompatibility Complex (MHC) binding and non-binding peptides compiled from published literature and existing databases. The database has sequence and structure data of (a) source proteins of peptides and (b) MHC molecules. MHCBN has a number of web tools that include: (i) mapping of peptide on query sequence; (ii) search on any field; (iii) creation of data sets; and (iv) online data submission (Bhasin et al., 2003, Bioinformatics 19(5): 665-666). In certain embodiments, the MHCBN is used to design a complex set of peptide-cDNA conjugates (or other peptide-polynucleotide conjugates) of the present invention. In preferred embodiments, the Immune Epitope Database (IEDB) is used to design a complex set of peptide-cDNA conjugates (e.g. >200) with known binding across all listed human HLA molecules. Binding studies for 207 human class II HLA molecules are listed in the IEDB. This set of "eigenpeptides" can be selected so that each member binds as narrow a set of HLA molecules as possible, thus providing both range and specificity (illustrated in FIG. 2). This peptide set can be tested against HLA class II molecules isolated from peripheral blood mononuclear cells (PBMCs) from healthy donors of known HLA types. This analysis allows the identification of a panel of reference peptides with binding across many HLA genotypes, which then serves as a useful internal normalization set for studies using peptide sets of higher complexity.

In one embodiment of the invention, the MHC-binding peptide is from a library of candidate antigenic peptides, wherein the each of the peptides in the library comprises conserved amino acids in a specific sequence sufficient to enable the peptide to bind to the peptide binding groove of an MHC molecule. In a more specific embodiment, the MHC-binding peptide is from a library of candidate antigenic peptides, wherein each of the peptides in the library comprises between about 4 and 5 conserved amino acids in a specific sequence sufficient to enable the peptide to bind to the peptide binding groove of an MHC molecule.

In one embodiment, a library of candidate peptides (candidate antigenic peptides or MHC-binding peptides) is produced by genetically engineering the library using polymerase chain reaction (PCR) or any other suitable technique to construct a DNA fragment encoding the peptide. With PCR techniques, by using oligonucleotides that are randomly mutated within particular triplet codons, the resultant fragment pool encodes all possible combination of codons at these positions. Preferably, certain of the amino acid positions are maintained constant, which are the conserved amino acids that are required for binding to the MHC peptide binding groove and which do not contact the T cell receptor.

iii. Implications of MHC and MHC Binding Peptides in Diseases

Peptide-MHC binding is generally related to immune activity and/or inactivity, and thereby has implications in a wide range of conditions and diseases, including but not limited to inflammation, allergy, autoimmune diseases, various types of cancers, and infection (viral or bacterial). Patients with diseases associated with immunosuppression, such as cancer, may benefit from strategies to remove immunosuppression and/or enhance tumor-specific immune response. In one aspect, the cancer is a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, or uterus. On the contrary, patients with diseases associated with heightened immune activity, such as inflammation, autoimmunity, allergy, and asthma, may benefit from strategies to down-regulate immune responses. In certain embodiments, the autoimmune disease is Addison's Disease, autoimmune hemolytic anemia, autoimmune inner ear disease, autoimmune lymphoproliferative syndrome, autoimmune thrombocytopenic purpura, autoimmune hemolytic anemia, autoimmune hepatitis, autoimmune oophoritis, Behcet's disease, autoimmune bullous pemphigoid, autoimmune cardiomyopathy, Crohn's disease, autoimmune chronic fatigue syndrome, chronic obstructive pulmonary disease (COPD), including chronic bronchitis, emphysema and chronic asthmatic bronchitis, autoimmune dermatomyositis, autoimmune diabetes mellitus type-1, autoimmune epilepsy autoimmune, Kawasaki's disease, autoimmune glomerulonephritis, Grave's disease, Goodpasture's syndrome, Guillain-Barré syndrome, lupus nephritis, multiple sclerosis, myasthenia gravis, autoimmune myocarditis, autoimmune Parkinson diseases, pediatrics autoimmune neuropsychiatry disorders, autoimmune pemphigus/pemphigoid, autoimmune pernicious anemia, autoimmune polyarteritis nodosa, autoimmune polymyositis, autoimmune primary biliary cirrhosis, psoriasis, autoimmune rheumatic fever, rheumatoid arthritis, autoimmune sarcoidosis, scleroderma, Sjogren's syndrome, autoimmune thyroiditis, autoimmune ulcerative colitis, autoimmune uveitis, autoimmune vitiligo, Wegener's granulomatosis, or Wilson's disease.

The peptides identified using methods of the present invention may have significantly lower, lower, the same, about the same, higher, or significantly higher binding affinities and/or specificities to an MHC molecule, when compared to a reference. The reference can be a binding affinity and/or specificity to a particular MHC molecule detected in a control normal subject, or in a control normal tissue or cell of a patient, or in a population of such control normal subjects or control normal tissues or cells. Depending on the needs of a patient, the peptides identified using methods of the present invention may be used to enhance, suppress, or regulate immune response in the patient.

The importance of the peptide-MHC complex in determining immune outcomes is also demonstrated by the large and increasing number of human genome-wide association studies that have strongly linked the genomic HLA locus to outcomes as diverse as autoimmunity (Wong and Wen, 2003, Curr. Mol. Med. 3: 1-15; Fernando et al., 2008, PLoS Genet. 4: e1000024; Handunnetthi et al., 2010, Genes Immun 11: 99-112), allergy (Marsh et al., 1973, Science 179: 691-693; Moffatt et al., 2010, N. Engl. J. Med. 363: 1211-1221), susceptibility to infection (International HIV Controllers Study, 2010, Science 330: 1551-1557) and drug reaction (Daly et al., 2009, Nat Genet. 41:816-819; Chung et al., 2004, Nature 428: 486; Hung, 2005, Proc. Natl. Acad. Sci. USA. 102: 4134-4139). Particular alleles of the MHC have been associated with a variety of diseases, including autoimmune diseases such as multiple sclerosis (MS), rheumatoid arthritis (RA), pemphigus vulgaris (PV), and systemic lupus erythematosus (SLE). It has been suggested that particular MHC proteins "improperly" recognize processed self peptides presented to T cells in the form of complexes with MHC Class I or Class II molecules. For example, susceptibility of MS is associated with the MHC class II region, and particular MHC class II haplotypes confer an increased risk of MS. The strongest association is with the HLA-DR2 haplotype (DRB1*1501). HLA-DR2 (encoded by the DRA, DRB 1*1501 genes) has been shown to present at least two peptides of human myelin basic protein (residues 85-99 and 148-162) to T cells. The MBP(85-99) peptide binds with high affinity to purified DR2, and the affinity of the MBP(148-162) peptide is lower but significant.

Underlying these associations is the fact that inter-individual variation in the HLA is extreme: each HLA haplotype encodes 3 class I and 3 class II complexes, these haplotypes are co-dominantly expressed and represent the most polymorphic loci in the genome. In total, this variation results in >104 different possible HLA class I and II molecules, ~12 of which will occur in any given individual. This complexity provides broad protection at the population level, ensuring that at least some members of the population have the capacity to present antigens from a given pathogen threat. However, a corollary is that there exists substantial inter-individual heterogeneity in the spectrum of antigen peptides that can be presented to T cells, resulting in a corresponding heterogeneity in immune responses. Addressing this heterogeneity is a key objective of personalized medicine and the present invention.

Since the present invention provides methods for understanding which peptides are recognized by a given MHC molecule, and which peptides are presented by a subject to elicit an immune response, one of skill in the art would appreciate that the methods disclosed herein are useful for a variety of purposes, including: (a) to identify peptide epitopes for the purpose of vaccine design; (b) to enable identification and monitoring of specific T cell responses against viruses, autoantigens, allergens; (c) to identify novel antigens in infection, autoimmunity, allergy, or cancer; (d) to test the potential immunogenicity of protein-based therapeutics.

C. Polynucleotide-Peptide Conjugates

The polynucleotide-peptide conjugate of the invention includes an oligonucleotide or a polynucleotide, used herein interchangeably, which may be a part of a larger nucleotide construct such as a plasmid. In certain embodiments, the polynucleotide can be an oligonucleotide, a modified oligonucleotide and oligonucleoside, alone or as part of a larger construct. The polynucleotide may be single-stranded DNA (ssDNA), double-stranded DNA (dsDNA), single-stranded RNA (ssRNA) or double-stranded RNA (dsRNA). In one aspect, the polynucleotide portion can be linearly or circularly configured, or the oligonucleotide portion can contain both linear and circular segments. Modifications of oligonucleotides include, but are not limited to, modifications of the 3'OH or 5'OH group, modifications of the nucleotide base, modifications of the sugar component, and modifications of the phosphate group.

The polynucleotide of the polynucleotide-peptide conjugate of the invention may comprise ribonucleotides (containing ribose as the only or principal sugar component), deoxyribonucleotides (deoxyribose as the principal sugar component), or in accordance with established state-of-the-art modified sugars or sugar analogs may be incorporated in the oligonucleotide of the present invention. Thus, in addition to ribose and deoxyribose, the sugar moiety may be pentose, deoxypentose, hexose, deoxyhexose, glucose, arabinose, xylose, lyxose, and a sugar "analog" cyclopentyl group. The sugar may be in pyranosyl or in a furanosyl form. The preparation of these sugars or sugar analogs and the respective "nucleosides" wherein such sugars or analogs are attached to a heterocyclic base (nucleic acid base) per se is known.

The phosphorous derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate, phosphorodithioate or the like. The preparation of the above-noted phosphate analogs, and their incorporation into nucleotides, modified nucleotides and oligonucleotides, per se, is also known.

The heterocyclic bases, or nucleic acid bases which are incorporated in the oligonucleotide base of the polynucleotide-peptide conjugate of the invention may be the naturally occurring principal purine and pyrimidine bases, (namely uracil or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) have become available in the art.

Without being bound by any theory, the probe that specifically binds to the polynucleotide of the polynucleotide-peptide conjugate of the invention may also be any natural or modified polynucleotide or derivative as described in any embodiments disclosed herein or any combinations thereof.

A variety of methods can be used to conjugate a polynucleotide to a candidate MHC-binding peptide. For example, as described in Example 1, peptide-cDNA conjugates can be produced from DNA molecules by either CoA-mediated formation or puromycin-mediated formation. Each method can be implemented at high plexity, for example by using high-complexity microarrays as a source of DNA templates. To this end, one approach is by multimerization or oligomerization of the polynucleotide-peptide conjugate. Any methods known to one of skill in the art as suitable for the present invention can be used. For example, as described in Example 2, multivalent peptide-cDNA conjugate molecules can be obtained through multimerization mediated by multivalent adapters, or multimerization through hybridization of the polynucleotides. These approaches for multimerization of polynucleotide-peptide conjugates can also be implemented in conjunction with each other to enable even higher order multiplexing.

Figures 3A, 3B:
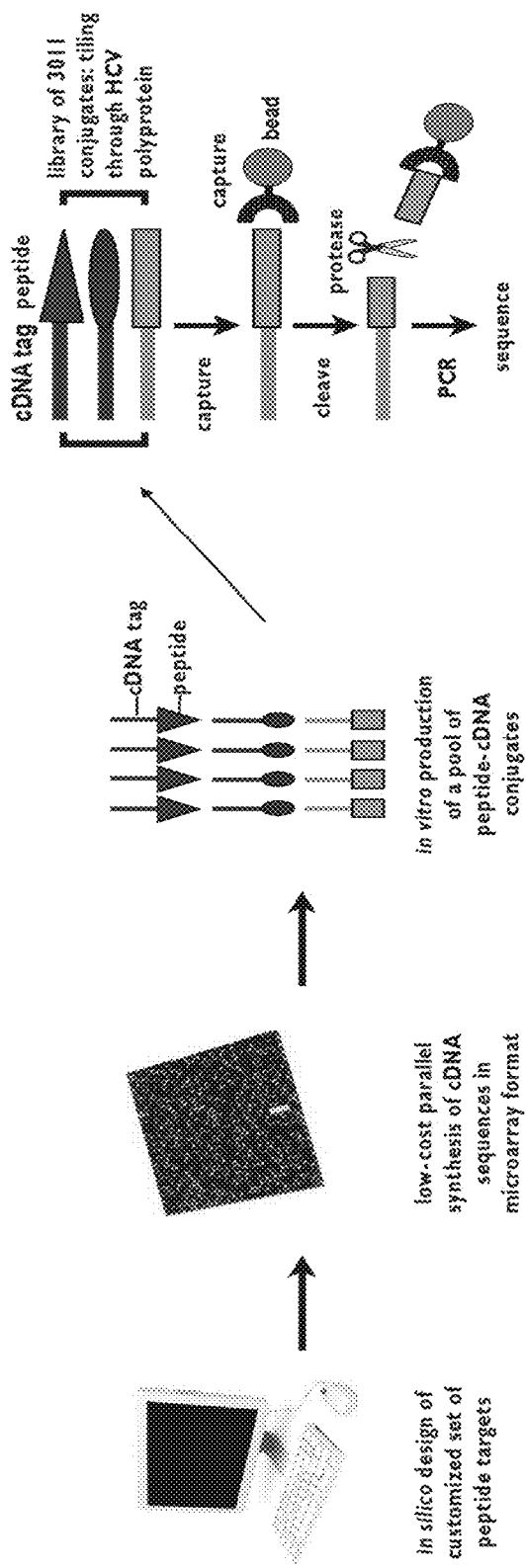
FIG. 3A shows a representative method for peptide-cDNA pool production. Oligonucleotide sequences of choice are designed in silico, cheaply produced by parallel synthesis on an array, released, and then converted into peptide-cDNA conjugates.
FIG. 3B shows a protease assay. Peptide-cDNA conjugate pools are immobilized on beads, treated with a protease, and the cleaved species are detected by sequencing of the released cDNAs.

In another embodiment, an inexpensive parallel oligonucleotide synthesis method is used. A large pool of in silico-designed DNA templates are synthesized, each containing a T7 promoter, ribosomal binding site, sequences coding for N- and C-terminal peptide tags, and a variable region coding for custom peptide sequences. These oligonucleotides are then transcribed and translated in vitro, using a process in which each translated peptide becomes covalently coupled to its encoding RNA, which is subsequently reverse-transcribed into cDNA. A schematic overview of the pool production process illustrating its intrinsically parallel and scalable nature is shown in FIG. 3A. The production of pools of several thousand peptide-cDNA conjugates tiling through the Hepatitis C Virus (HCV) polyprotein and their utility in assaying the activity of HCV NS3/4A protease are shown in FIG. 3B and described in more detail in Shiryaev et al, 2012, PLoS ONE 7(4): e35759.

In preferred embodiments, the polynucleotide-peptide conjugate of the present invention is not associated, complexed, or conjugated with, or otherwise immobilized to any surface, membrane, or the like before contacting an MHC molecule. For example, in one aspect, the polynucleotide-peptide conjugate of the present invention, including a multimerized or oligomerized conjugate, is not associated, complexed, or conjugated with a cellular membrane or a viral particle. In one embodiment, the polynucleotide-peptide conjugate disclosed herein is not associated, complexed, or conjugated with a phage coat protein.

D. Methods of Detecting Peptide Binding to an MHC Molecule

Provided here are also methods for detecting binding of a candidate MHC-binding peptide to an MHC molecule. In preferred embodiments, detection of competitive binding of a pool or library of multiple candidate MHC-binding peptides to a particular MHC molecule is accomplished by the present invention. In one embodiment, a scalable, multiplexed, competition-based binding assay capable of testing large, customizable peptide sets across all of an individual's HLA class II molecules, is provided. For a given MHC molecule, the ability to detect binding of multiple candidate MHC-binding peptides at the same time, and to compare their relative binding affinity and/or specificity to the MHC molecule, makes the present invention particularly useful for the diagnosis, treatment, and/or prognosis of human diseases.

In one embodiment, a method for detecting binding of a peptide to an MHC molecule is disclosed. The method comprises: contacting said MHC molecule with a polynucleotide-peptide conjugate, said polynucleotide-peptide conjugate comprising said peptide and a polynucleotide; contacting said polynucleotide-peptide conjugate with a probe that specifically binds to said polynucleotide; detecting binding of said probe to said polynucleotide; and, correlating binding of said probe to said polynucleotide with binding of said peptide to said MHC molecule.

In another embodiment, a method for simultaneously detecting binding of a library of peptides to an MHC molecule is provided. The method comprises: providing a polynucleotide-peptide conjugate for each said peptide, said polynucleotide-peptide conjugate comprising said peptide and a polynucleotide; contacting said MHC molecule with a pool of said polynucleotide-peptide conjugates; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said MHC molecule. In another embodiment, the method further comprises comparing binding of each said peptide to said MHC molecule, among the peptides in said library.

In yet another embodiment, provided herein is a method for detecting in a library of peptides competitive binding of each said peptide to an MHC molecule, comprising: providing a polynucleotide-peptide conjugate for each said peptide, said polynucleotide-peptide conjugate comprising said peptide and a polynucleotide; contacting said MHC molecule with a pool of said polynucleotide-peptide conjugates; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said MHC molecule, wherein said peptides compete for binding of said MHC molecule. In another embodiment, the method further comprises comparing binding of each said peptide to said MHC molecule, among the peptides in said library.

In one embodiment, the method disclosed herein is used in a multiplexed peptide-MHC binding assay. As shown in FIG. 1 (upper panel), MHC molecules are tested in a pooled binding reaction against a set of in silico-programmed peptide-cDNA conjugates. Bound peptides are identified by high throughput DNA sequencing, which has the dynamic range to reveal the spectrum of differentially-competitive MHC binders.

In any of the foregoing method embodiments or any combination thereof, an MHC molecule can be contacted with a polynucleotide-peptide conjugate first, followed by washing away of unbound conjugate, and then the MHC-conjugate complex is contacted with a probe specific for the polynucleotide. In another embodiment, a polynucleotide-peptide conjugate can be contacted with a probe first, before the mixture is contacted with an MHC molecule. In yet another embodiment, an MHC molecule can be contacted with a polynucleotide-peptide conjugate and a probe at about the same time, and the polynucleotide-peptide conjugate does not need to contact the probe first.

In one embodiment, the MHC molecule is immobilized to a carrier. The carrier can be a molecule, particle, composition, or other microscopic object to which may be conjugated, directly or indirectly, at least one MHC molecule, and in preferred embodiments, a multiplicity of MHC molecules. In certain embodiments, the carrier refers to the backbone of the conjugate, on which various molecules may be attached. In particular examples, the carrier comprises water-soluble polymers, including but are not limited to natural and synthetic polysaccharides, as well as derivatives thereof, for example dextrans and dextran derivatives, starches and starch derivatives, cellulose derivatives, amylose and pectin, as well as certain natural gums and derivatives thereof, such as gum arabic and salts of alginic acid; homopoly(amino acid)s having suitable reactive functionalities, such as polylysines, polyhistidines or polyornithines; natural and synthetic polypeptides and proteins, such as bovine serum albumin, immunoglobulins, and other mammalian albumins; and synthetic polymers having nucleophilic functional groups, such as polyvinyl alcohols, polyallyl alcohol, polyethylene glycols and substituted polyacrylates.

In certain embodiments, the carrier is a molecule. In other embodiments, the carrier is a surface. The surface can be a plastic surface, or a surface comprised in a nitrocellulose membrane, a nylon membrane, a latex particle, or a gold particle. In certain embodiments, the MHC molecule is biotinylated and the carrier is modified with streptavidin. The MHC molecule and the carrier can be otherwise modified for use in the present invention.

In some embodiments, the carrier is biodegradable, the carrier is non-immunogenic, the carrier has a net neutral or negative charge, and/or the carrier is fluorescently labeled. The carrier may be covalently or non-covalently bound to a surface, such as a plastic surface, or a surface comprised in a nitrocellulose membrane, a nylon membrane, a latex particle, or a gold particle. In some embodiments, the carrier is a substantially spherical bead or a porous bead. In certain embodiments in which the carrier is a bead, the bead preferably comprises a material selected from the group consisting of glass, silica, polyesters of hydroxy carboxylic acids, polyanhydrides of dicarboxylic acids, or copolymers of hydroxy carboxylic acids and dicarboxylic acids. In some embodiments, the carrier is a branched polymer, such as a dendrimer. In preferred embodiments when the carrier is a dendrimer, the dendrimer comprises a material selected from the group consisting of a polyamidoamine, a polyamidoalcohol, a polyalkyleneimine, a polyalkylene, a polyether, a polythioether, a polyphosphonium, a polysiloxane, a polyamide, and a polyaryl polymer.

In some embodiments, the MHC molecule/carrier complex further comprises a linker. A linker can be a bi-functional molecule capable of establishing covalent links between other molecules. Examples of bi-functional molecules suitable as linkers include but are not limited to glutaraldehyde, carbodiimides, N,N'-phenylenedimaleimide, N-succinimidyl 3-(2-pyridylthio)propionate, p-benzoquinone, divinyl sulfone (DVS) and epoxide derivatives such as epichlorohydrin and other epoxide derivatives described in U.S. Pat. No. 6,627,460, incorporated herein by reference. Preferably, the linking component should be stable in an aqueous environment. In some embodiments, the MHC molecule/carrier complex further comprises a spacer. A spacer can be a protein or a polypeptide having a plurality of sites available for covalent attachment of other components. Although not necessary for practicing the invention, a spacer may provide a suitable means of increasing the number of cobinamide moieties which can be attached to the conjugate, thereby increasing the sensitivity of such conjugates when employed in various assays. Examples of protein spacers include but are not limited to bovine serum albumin, ovalbumin, globulin, etc. Examples of polypeptide spacers include but are not limited to homopolypeptides, such as polylysines, polyhistidines, polyornithines, etc. As will be clear to a person skilled in the art, the choice of spacer will depend on the employed MHC molecule, the employed carrier, as well as the employed linking component. In some aspects, the spacer component can be a polysaccharide or polynucleic acid. Chemical modifications of these polymers may be required prior to the preparation of the water-soluble intermediate conjugate.

In a preferred embodiment, the pools of peptides bearing unique polynucleotide tags (e.g., DNA-tags) allow many peptides to be tested for binding in a single reaction and reported by high throughput sequencing. Advantages of the present polynucleotide-conjugate based assay approach include:

(a) Defined content. Bioinformatically-defined oligonucleotide sequences of choice are produced by parallel synthesis on an array, and then converted into the corresponding cDNA-peptide conjugates. The system can be readily programmed to display peptides from any immunogen of choice. For example, the present inventors have already synthesized and validated in protease assays sets of peptide-cDNA conjugates that tile through the 3,011 amino acid HCV proteome with a step resolution of 1 amino acid (Kozlov et al., 2012, PLoS One 7:e37441).

(b) Intrinsic, competition-based multiplexing. The proteolytic processes of the proteasome (for class I) and endosome (for class II) give rise to complex peptide milieus, and the present inventors have utilized the peptide-peptide competition for MHC binding. In one embodiment, the present invention provides a biologically relevant way to increase the plexity of a peptide-MHC binding assay by a solution-phase approach, where inter-peptide competition is possible, rather than an immobilized peptide approach. In one aspect, the present invention provides methods to narrow a large number of peptides found to bind an MHC molecule, for example, those in published peptide microarray studies (Gaseitsiwe et al., 2009, Clin Vaccine Immunol. 16: 567-573; Gaseitsiwe et al., 2010, Clin Vaccine Immunol. 17: 168-175), to the best binders.

(c) Next generation sequencing readout. Among other advantages, next generation sequencing has high sensitivity, allowing binders to be detected among large peptide pools.

In one embodiment, peptide-cDNA conjugates are used as multiplex probes for MHC binding. For example, in Example 3, the MHC class II molecules HLA-DR3 and HLA-DR1 were biotinylated and immobilized on streptavidin beads, and two peptides known to bind HLA-DR3 and HLA-DR1, respectively, without cross-binding, were used to bind the MHC class II molecules. The peptide-cDNA conjugates comprising the two peptides were detected by gel electrophoresis and quantitative polymerase chain reaction for the polynucleotide portions of the conjugates. The results indicate that each conjugate bound to the expected MHC molecule but not to the other HLA-DR family member. In another example, three peptides known to bind the HLA-DR1 molecule with high, high, and low affinities, respectively, were used. The results indicate the expected profile of binding for the three conjugates (high, high, low), both in the case where conjugates were present individually (1-plex), and in the case where the conjugates were incubated and detected as a mixture (3-plex).

In one embodiment, multiplexing of the peptide-MHC binding assay across multiple peptides is performed using the next-generation sequencing readout. For example, 45 candidate peptides can be chosen from the proteome of influenza A virus on the basis that they are conserved across different strains and predicted to bind the majority of common HLA-DR molecules. Peptide-cDNA-conjugates corresponding to these 45 sequences can be prepared and incubated with recombinant biotinylated HLA-DR3. In this example, HLA-DR3 is selected as a representative HLA molecule because it is one to which binding of the 45 peptides has been measured, with a wide range of binding affinities for the different peptides. Without being bound by any theory, other MHC molecules may be used. The reported binding affinities of the 45 peptides to the MHC molecule can be used as reference. In one embodiment, the signals obtained for these 45 peptides in multiplex and single-plex assays are compared with their reported binding affinities. In one aspect, the method of the present invention provides a comprehensive data matrix that includes known positives and negatives, serving as an ideal system to test and optimize new assay format.

In preferred embodiments, the method disclosed herein is competition-based. In preferred embodiments, the method disclosed herein uses a sequencing readout. As such, in certain embodiments, the type of data generated by methods of the invention differs considerably from what has been generated in single-plex binding experiments, or even peptide microarray experiments. In one embodiment, the multiplexed competitive binding format manifests as a strongly skewed representation of the starting peptides according to their binding affinity. As well as allowing the best binders to be identified from the pool, in certain aspects, lower affinity binders are discriminated from non-binders, for example, thanks to the high sensitivity and large dynamic range of next generation sequencing. In preferred embodiments, lower affinity binders are discriminated from non-binders, and simultaneously the best binders are also identified from the pool. In one embodiment, the methods disclosed herein are used in conjunction with previously reported affinities, for example, to develop analysis approaches that can relate sequence abundance with binding affinity.

In one embodiment, peptide-MHC binding assays to HLA sets isolated from human samples, for example, human blood samples, are performed. In another embodiment, peptide-MHC binding assays are performed to identify personalized pathogen epitopes. In one aspect, a multiplexed peptide-MHC binding assay method is used for defined recombinant HLA molecules. In another aspect, a multiplexed peptide-MHC binding assay method is used for bulk genotype-based sets of HLA molecules isolated from human blood. Protocols for the isolation of HLA molecules from primary human cells are established (Fissolo et al., 2009, Mol. Cell Proteomics. 8: 2090-2101), however the preference for transfected cells or cell lines as sources of HLA molecules reflects the fact that traditional assay formats require large quantities of single HLA species. In contrast, for a multiplexed assay read-out by sensitive next generation sequencing, there is no need to isolate single MHC-peptide pairs. In a preferred embodiment, the method disclosed herein does not require isolation of single MHC-peptide pairs. In one embodiment, the method disclosed herein is sensitive and requires significantly less HLA material. In one example, the binding of peptide-cDNA conjugates to sets of HLA class II molecules derived from the peripheral blood mononuclear cells (PBMCs) of anonymous human donors is detected. PBMCs represent a readily-available biological sample type, and one in which HLA class II proteins are abundantly expressed. In certain aspects, the method comprises: (a) incubating polynucleotide-peptide conjugates with cells; lysing cells; immunoprecipitating HLA molecules; eluting the conjugates; or (b) lysing cells; immunoprecipitating HLA molecules; incubating polynucleotide-peptide conjugates with cells; eluting the conjugates; or (c) incubating polynucleotide-peptide conjugates with cells; eluting peptides from cells directly. In one aspect, the 45 influenza encoded peptides described above for binding to the HLA molecules of 10 influenza reactive human donors are used. In one embodiment, a snapshot of the influenza:HLA class II "presentome" for each of the donor individuals are provided. In some embodiments, such a snapshot can be a profile of which peptides can be presented by which donor but not by others. In some embodiments, the binding profiles are then compared with two orthogonal sources of information about the donors' influenza epitopes: (i) T cell reactivity profiles of the 10 donors for the same 45-peptide set, generated using the traditional ELISpot assay, and (ii) the HLA genotypes of the 10 donors, crossmatched with the published binding affinities of the peptides for 17 individual HLA-DR molecules.

In one aspect, an application of the peptide-MHC binding assays disclosed herein is the prediction of epitopes that are recognized by T cells during an immune response, in particular, during a T cell response. Although the ability to interact with MHC is one of several factors necessary for a peptide to generate a T cell response (other key factors being proteolytic production of the peptide, and availability of binding T cells within the T cell repertoire), there is evidence that MHC interaction has a large effect and can be powerfully predictive.

At equilibrium, biomolecular binding is a function of both association (the rate at which the molecules become bound with each other) and dissociation (the rate at which the molecules detach from each other). In some aspects, binding assays report how much binding is present at equilibrium (a convolution of both association and dissociation). In other aspects, however, slow dissociation of a particular peptide-MHC complex is an independent and key requirement for a peptide to elicit a T cell response. See for example, Yin et al., "HLA-DM constrains epitope selection in the human CD4 T cell response to vaccinia virus by favoring the presentation of peptides with longer HLA-DM-mediated half-lives," *J Immunol.* 2012, 189:3983-94. See also Lazarski et al., "The kinetic stability of MHC class II:peptide complexes is a key parameter that dictates immunodominance," *Immunity* 2005, 23:29-40. The disclosures of these references are incorporated herein by reference in their entireties for all purposes.

In one aspect, disclosed herein is a method of detecting specific binding of a polypeptide to an MHC molecule, comprising setting up an equilibrium between a polynucleotide-peptide conjugate (the peptide-bearing probe) and the MHC molecules, washing away unbound polynucleotide-peptide conjugate molecules, and leaving the loaded MHC complexes to dissociate for a period of time (e.g., ≥about 30 minutes, 1 hour, 2 hours, 3 hour, 4 hours, 5 hour, 6 hours, 7 hour, 8 hours, 9 hour, 10 hours, 11 hour, 12 hours, 13 hours, 14 hours, 15 hours, or about 16 hours), optionally in the presence of one or more blocker species that binds MHC but does not generate signal, and then assaying the polynucleotide-peptide conjugates that remain bound to the MHC molecules. In one embodiment, the one or more blocker species compete with the peptide moieties of the polynucleotide-peptide conjugates in binding to the MHC molecules, thereby preventing peptide reassociating with the MHC molecule.

In any of the embodiments disclosed herein, chemical chaperones can be added before, during, or after allowing the polynucleotide-peptide conjugates to bind to the MHC molecules. In one aspect, physiological peptide-MHC binding occurs in the presence of a protein chaperone (e.g., HLA-DM) that facilitates peptide loading and unloading onto MHC molecules and acts to shape the repertoire of peptides that bind MHC and are responded to by T cells. In one aspect, the biological utility of the multiplexed peptide:MHC assay disclosed herein can be improved by the addition of chaperones that recapitulate this function, such as recombinant HLA-DM and small molecule chaperones that have the same or similar effects. These include parachlorophenol (pCP) or dimethylsulphoxide (DMSO). See Marin-Esteban et al., J Biol Chem. 2004, 279:50684-90, which discloses that chemical analogues of HLA-DM can induce a peptide-receptive state in HLA-DR molecules. The disclosure of Marin-Esteban et al. is incorporated herein by reference in its entirety for all purposes.

E. Methods of Detecting Peptide Binding to a TCR or a T Cell

Provided here are also methods for detecting binding of a candidate MHC-binding peptide to a TCR or a T cell. In preferred embodiments, detection of competitive binding of a pool or library of multiple candidate MHC-binding peptides to a particular MHC molecule/TCR combination is accomplished by the present invention. In one embodiment, a polynucleotide-peptide conjugate (e.g., peptide-cDNA conjugate) is bound to MHC molecules as probes for the multiplexed detection of specific T cells. In one aspect, the polynucleotide-peptide conjugate is multimerized or oligomerized.

In one aspect, disclosed herein is a method for detecting binding of a peptide to a T cell, comprising: contacting said T cell with an MHC molecule an a polynucleotide-peptide conjugate, said polynucleotide-peptide conjugate comprising said peptide and a polynucleotide; contacting said polynucleotide-peptide conjugate with a probe that specifically binds to said polynucleotide; detecting binding of said probe to said polynucleotide; and, correlating binding of said probe to said polynucleotide with binding of said peptide to said T cell.

In another aspect, a method for simultaneously detecting binding of a library of peptides to a T cell is provided. This method comprises: providing a polynucleotide-peptide conjugate for each said peptide, said polynucleotide-peptide conjugate comprising said peptide and a polynucleotide; contacting said T cell with a pool of said polynucleotide-peptide conjugates and an MHC molecule; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said T cell. In one embodiment, the peptide of the present invention binds a TCR of said T cell.

In yet another aspect, described herein is a method for detecting in a library of peptides competitive binding of each said peptide to a T cell, comprising: providing a polynucleotide-peptide conjugate for each said peptide, said polynucleotide-peptide conjugate comprising said peptide and a polynucleotide; contacting said T cell with a pool of said polynucleotide-peptide conjugates and an MHC molecule; contacting each of said polynucleotide-peptide conjugate with a probe that specifically binds to each said polynucleotide; detecting binding of said probe to each corresponding polynucleotide that each said probe specifically binds; and correlating binding of said probe to each corresponding polynucleotide with binding of each corresponding peptide to said T cell, wherein said peptides compete for binding of said MHC molecule and said T cell. In one embodiment, the peptide binds a TCR of said T cell.

In any of the embodiments disclosed herein or any combination thereof, the method of the present invention can further comprise comparing the detected binding of said peptide to said MHC molecule or said T cell with a reference. In a further embodiment, the method of the present invention as disclosed in any embodiments or any combination thereof further comprises selecting the detected binding of said peptide over the reference, for the purposes of identifying antigens in infection, autoimmunity, allergy, or cancer, or for vaccine design.

In any of the foregoing method embodiments or any combination thereof, an MHC/TCR pair can be contacted with a polynucleotide-peptide conjugate first, followed by washing away of unbound conjugate, and then the MHC-TCR-conjugate complex is contacted with a probe specific for the polynucleotide. In another embodiment, a polynucleotide-peptide conjugate can be contacted with a probe first, before the mixture is contacted with an MHC/TCR pair. In yet another embodiment, an MHC/TCR pair can be contacted with a polynucleotide-peptide conjugate and a probe at about the same time, and the polynucleotide-peptide conjugate does not need to contact the probe first.

In any of the embodiments disclosed herein or any combination thereof, the polynucleotide and the probe are selected from the group consisting of DNA, cDNA, RNA, mRNA, rRNA, tRNA, PNA, a DNA-like molecule or an RNA-like molecule. In any of the embodiments disclosed herein or any combination thereof, the binding of said probe to said polynucleotide can be detected by gel electrophoresis, hybridization, PCR, qPCR, or nucleotide sequencing.

A challenge inherent in the use of binding probes to detect specific T cells is the low binding affinity between the peptide:MHC complex and the TCR. Here, in one embodiment, the polynucleotide-peptide conjugate is multimerized or oligomerized, which overcomes the low binding affinity issue. In one embodiment, branched adapter molecules are used to produce multivalent conjugates in which several identical peptides are covalently linked to a single identifying DNA tag. In one aspect, conjugates that each contain two identical peptides are produced and detected. This approach can be readily adapted to higher order multiplexing in preferred embodiments. In another preferred embodiment, the method is performed in a high throughput fashion.

In one example, T cell lines HA1.7 and 131.5 are used. HA1.7 and 131.5 are known to recognize the peptides PKYVKQNTLKLAT (SEQ ID NO: 6) and QYIKANSK-FIGITE (SEQ ID NO:7), respectively, in complex with HLA-DR1 (Hennecke and Wiley, 2002, J Exp Med. 4: 571-581; De Magistris et al., 1992, Cell. 68: 625-634). Cconjugates with sequences PKYVKQNTLKLAT (SEQ ID NO: 6) and QYIKANSKFIGITE (SEQ ID NO: 7) are prepared at valencies of 1, 2 and 4. The conjugates are then incubated together with recombinantly-expressed HLA-DR1. In addition, HA1.7 and 131.5 T cells are added to the binding reactions, either from the outset or after an initial period of peptide-MHC binding. After incubation, cells are washed to remove unbound species (these could include conjugates, MHC molecules, and MHC:conjugate complexes) and then the bound conjugates eluted and detected by their cDNA tags. In one embodiment, after establishing a T cell detection capability, two T cell lines are combined in different ratios to confirm the sensitivity and multiplexity of the assay. In another embodiment, both types of conjugates are applied simultaneously as detectors to confirm the sensitivity and multiplexity of the assay.

In the method of the invention, the T cell receptor can be a T cell receptor for which it is desired to identify the peptide epitope recognized by the receptor. In one aspect, the T cell receptor is from a patient with a T cell-mediated disease, such as an autoimmune disease or a hyperproliferative disease. In other embodiments, the target T cell receptor is from a patient with a different condition, such as an infection by a pathogenic microorganism or a patient with cancer. Knowledge of the antigen that is bound by a specified T cell can have therapeutic value for a variety of reasons. Preferably, the T cell receptor is an αβ T cell receptor. An αβ T cell (expressing an αβ T cell receptor) is a lineage of T lymphocytes found in mammalian species and birds that expresses an antigen receptor (i.e., a TCR) that includes an α chain and a β chain. Without being bound by any theory, the T cell receptor can be a γδ T cell receptor.

The T cell receptor can be expressed by a cell or provided as a soluble T cell receptor. In the former embodiment, the T cell receptor can be expressed by the T cell that naturally expresses the receptor (e.g., a T cell clone or hybridoma) or by another cell that recombinantly expresses the T cell receptor. In the latter embodiment, the soluble T cell receptor is preferably immobilized on a substrate or solid support for contact with the MHC and the polynulcoetide-peptide conjugate.

Briefly, a substrate or solid support refers to any solid organic supports, artificial membranes, biopolymer supports, or inorganic supports that can form a bond with a soluble T cell receptor without significantly affecting the ability of the T cell receptor to bind to an MHC-peptide complex for which the T cell receptor has specificity. Exemplary organic solid supports include polymers such as polystyrene, nylon, phenol-formaldehyde resins, acrylic copolymers (e.g., polyacrylamide). Exemplary biopolymer supports include cellulose, polydextrans (e.g., Sephadex™), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Soluble T cell receptors can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Cross-linking to a solid support involves forming a chemical bond between a solid support and the T cell receptor. Cross-linking commonly uses a bifunctional or multifunctional reagent to activate and attach a carboxyl group, amino group, sulfur group, hydroxy group or other functional group of the receptor to the solid support. Entrapment of involves formation of, inter alia, gels (using organic or biological polymers), vesicles (including microencapsulation), semipermeable membranes or other matrices, such as by using collagen, gelatin, agar, cellulose triacetate, alginate, polyacrylamide, polystyrene, polyurethane, epoxy resins, carrageenan, and egg albumin.

The target T cell receptor can be labeled with a detectable label. Detectable labels suitable for use include any compound detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

As used herein, "TCR recognition" or "TCR binding" refers to the ability of a TCR to bind to an MHC-peptide complex, wherein the level of binding, as measured by any standard assay (e.g., an immunoassay or other binding assay), is statistically significantly higher than the background control for the assay. Binding assays are well known in the art. For example, a BIAcore machine can be used to determine the binding constant of a complex between two proteins. The dissociation constant for the complex can be determined by monitoring changes in the refractive index with respect to time as buffer is passed over the chip. Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR).

In one embodiment, one can additionally measure whether a T cell receptor that is expressed by a T cell, when bound by an MHC-peptide complex produced by the invention, displays a T cell response to the binding. A T cell response occurs when a TCR recognizes an MHC protein bound to an antigenic peptide, thereby altering the activity of the T cell bearing the TCR. As used herein, a "T cell response" can refer to the activation, induction of anergy, or death of a T cell that occurs when the TCR of the T cell is bound by an MHC-peptide complex. As used herein, "activation" of a T cell refers to induction of signal transduction pathways in the T cell resulting in production of cellular products (e.g., interleukin-2) by that T cell. "Anergy" refers to the diminished reactivity by a T cell to an antigen. Activation and anergy can be measured by, for example, measuring the amount of IL-2 produced by a T cell after and MHC-peptide complex has bound to the TCR. Anergic cells will have decreased IL-2 production when compared with stimulated T cells. Another method for measuring the diminished activity of anergic T cells includes measuring intracellular and/or extracellular calcium mobilization by a T cell upon engagement of its TCRs. As used herein, "T cell death" refers to the permanent cessation of substantially all functions of the T cell. In the method of the present invention, the T cell will typically encounter the MHC-peptide complex in the absence of additional costimulatory signals that are normally required to induce T cell activation events. However, under some conditions, some type or level of T cell response will be measurable.

The ability of a T lymphocyte to respond to binding by an MHC-peptide complex can be measured by any suitable method of measuring T cell activation. Such methods are well known to those of skill in the art. For example, after a T cell has been stimulated with an antigenic or mitogenic stimulus, characteristics of T cell activation can be determined by a method including, but not limited to: measuring the amount of IL-2 produced by a T cell (e.g., by immunoassay or biological assay); measuring the amount of other cytokines produced by the T cell (e.g., by immunoassay or biological assay); measuring intracellular and/or extracellular calcium mobilization (e.g., by calcium mobilization assays); measuring T cell proliferation (e.g., by proliferation assays such as radioisotope incorporation); measuring upregulation of cytokine receptors on the T cell surface, including IL-2R (e.g., by flow cytometry, immunofluorescence assays, immunoblots); measuring upregulation of other receptors associated with T cell activation on the T cell surface (e.g., by flow cytometry, immunofluorescence assays, immunoblots); measuring reorganization of the cytoskeleton (e.g., by immunofluorescence assays, immunoprecipitation, immunoblots); measuring upregulation of expression and activity of signal transduction proteins associated with T cell activation (e.g., by kinase assays, phosphorylation assays, immunoblots, RNA assays); and, measuring specific effector functions of the T cell (e.g., by proliferation assays, cytotoxicity assays, B cell assays). Methods for performing each of these measurements are well known to those of ordinary skill in the art, and all such methods are encompassed by the present invention.

In one embodiment, methods disclosed in any embodiments or combinations thereof can be used for vaccine design or vaccine development. While vaccines are best established in the infectious disease context, development efforts have more recently broadened their focus to anti-tumor vaccines, as well as tolerogenic vaccines for the treatment of allergy and autoimmunity. Whereas traditional vaccines are based on whole pathogens (either killed or attenuated), modern approaches (so-called "second" and "third generation" vaccines) have focused on immunogen subunits (particular proteins or peptides), as these offer the major advantages of reduced risk, improved stability and, most importantly, the opportunity for more refined control over the immune response. The present invention provides methods for developing a successful subunit vaccine, that is, for selecting epitopes on the subunit(s) to be efficiently presented to T cells as MHC-bound peptides.

In one embodiment, the entire proteome of the immunogen of interest (e.g. bacterial or viral pathogen) is represented as peptide-cDNA conjugates. These conjugates are incubated, in a single binding pool, with HLA molecules from vaccinee populations (either at a representative level or, in a personalized medicine approach, at the individual level). The competitive binding reaction is then select the best binders from the pool, in a way that broadly mimics the natural antigen processing milieu in vivo, and these binders are reported in a sensitive and high-throughput fashion by next generation sequencing. The same approach could also be used to discover useful peptide-MHC tetramer combinations, and thereby provide ways to investigate and monitor T cell immune responses. In another embodiment, the methods disclosed herein are used for developing protein-based therapeutics, for example, for pre-screening therapeutics against patient HLA molecules, in order to avoid protein sequences with the potential to elicit adverse reactions.

In one aspect, the application of the peptide-MHC binding assay disclosed herein involves the use of genotype-based MHC sets derived from patient samples, e.g., peripheral blood from a patient or a normal control. Since the MHC molecules are cell surface-expressed proteins, in one aspect, the assay format involves using intact cells as a solid support capable of capturing and separating binding MHC-peptide probes, e.g., a polynucleotide-peptide conjugate disclosed herein. In one embodiment, the polynucleotide-peptide conjugates are incubated with cells, the cells are pelleted and washed to wash away unbound and/or non-specifically bound polynucleotide-peptide conjugates, and then the polynucleotide-peptide conjugates that remain bound to the cells after the washing are eluted and quantified. In some embodiments, all expressed MHC proteins on the surface of cells are available for the assay at their physiological abundances without the need for capture by a panel of MHC-binding antibodies. In other embodiments, the method disclosed herein avoids exposing internal cellular components to the polynucleotide-peptide conjugates (the peptide probes), which may bind non-specifically to the internal cellular components. In some embodiments, cell-surface components other than MHC molecules are removed, blocked, or masked, for example, to prevent non-specific binding to the polynucleotide-peptide conjugates. Peptide binding to cell-surface expressed MHC has been demonstrated in the art, see for example Ceppellini et al., "Binding of labelled influenza matrix peptide to HLA DR in living B lymphoid cells," *Nature* 1989, 339:392-4, the disclosure of which is incorporated herein by reference in its entirety for all purposes.

The following exemplary embodiments and examples are intended to further describe and illustrate various aspects of the invention, but not to limit, the scope of the invention in any manner, shape, or form, either explicitly or implicitly.

The present invention is further illustrated by the following exemplary embodiments:

1. An MHC-binding peptide conjugated to a polynucleotide.

2. A library of at least two MHC-binding peptides each conjugated to a polynucleotide, wherein each said polynucleotide is identified by a probe that specifically binds to said polynucleotide.
3. A composition comprising at least two MHC-binding peptides each conjugated to a polynucleotide, wherein the at least two MHC-binding peptides are multimerized or oligomerized.
4. The composition of embodiment 3, wherein the at least two MHC-binding peptides are conjugated to the same polynucleotide and are thus multimerized or oligomerized.
5. The composition of embodiment 3, wherein the at least two MHC-binding peptides are each conjugated to a separate polynucleotide, wherein the polynucleotides mediate the multimerization or oligomerization of the at least two MHC-binding peptides.
6. The composition of embodiment 5, wherein the mediation is through nucleotide sequence complementarity.
7. A method for detecting binding of a peptide to an MHC molecule, comprising:
contacting said MHC molecule with a polynucleotide-peptide conjugate, said polynucleotide-peptide conjugate comprising said peptide and a polynucleotide;
contacting said polynucleotide-peptide conjugate with a probe that specifically binds to said polynucleotide;
detecting binding of said probe to said polynucleotide; and
correlating binding of said probe to said polynucleotide with binding of said peptide to said MHC molecule.
8. A method for simultaneously detecting binding of a library of peptides to an MHC molecule, comprising:
providing a polynucleotide-peptide conjugate for each said peptide, said polynucleotide-peptide conjugate comprising said peptide and a polynucleotide;
contacting said MHC molecule with a pool of said polynucleotide-peptide conjugates;
contacting each of said polynucleotide-peptide conjugate with a probe that specifically binds to each said polynucleotide;
detecting binding of said probe to each corresponding polynucleotide that each said probe specifically binds; and
correlating binding of said probe to each corresponding polynucleotide with binding of each corresponding peptide to said MHC molecule.
9. A method for detecting in a library of peptides competitive binding of each said peptide to an MHC molecule, comprising:
providing a polynucleotide-peptide conjugate for each said peptide, said polynucleotide-peptide conjugate comprising said peptide and a polynucleotide;
contacting said MHC molecule with a pool of said polynucleotide-peptide conjugates;
contacting each of said polynucleotide-peptide conjugate with a probe that specifically binds to each said polynucleotide;
detecting binding of said probe to each corresponding polynucleotide that each said probe specifically binds; and
correlating binding of said probe to each corresponding polynucleotide with binding of each corresponding peptide to said MHC molecule,
wherein said peptides compete for binding of said MHC molecule.
10. A method of embodiment 8 or 9, further comprising comparing binding of each said peptide to said MHC molecule, among the peptides in said library.
11. A method of detecting binding of a peptide to a TCR, comprising:
contacting said TCR with an MHC molecule and a polynucleotide-peptide conjugate, said polynucleotide-peptide conjugate comprising said peptide and a polynucleotide;
contacting said polynucleotide-peptide conjugate with a probe that specifically binds to said polynucleotide;
detecting binding of said probe to said polynucleotide; and
correlating binding of said probe to said polynucleotide with binding of said peptide to said TCR.
12. A method for simultaneously detecting binding of a library of peptides to a TCR, comprising:
providing a polynucleotide-peptide conjugate for each said peptide, said polynucleotide-peptide conjugate comprising said peptide and a polynucleotide;
contacting said TCR with a pool of said polynucleotide-peptide conjugates and an MHC molecule;
contacting each of said polynucleotide-peptide conjugate with a probe that specifically binds to each said polynucleotide;
detecting binding of said probe to each corresponding polynucleotide that each said probe specifically binds; and
correlating binding of said probe to each corresponding polynucleotide with binding of each corresponding peptide to said TCR.
13. A method for detecting in a library of peptides competitive binding of each said peptide to a TCR, comprising:
providing a polynucleotide-peptide conjugate for each said peptide, said polynucleotide-peptide conjugate comprising said peptide and a polynucleotide;
contacting said TCR with a pool of said polynucleotide-peptide conjugates and an MHC molecule;
contacting each of said polynucleotide-peptide conjugate with a probe that specifically binds to each said polynucleotide;
detecting binding of said probe to each corresponding polynucleotide that each said probe specifically binds; and
correlating binding of said probe to each corresponding polynucleotide with binding of each corresponding peptide to said TCR,
wherein said peptides compete for binding of said MHC molecule and said TCR.
14. The method of any one of embodiments 11-13, wherein said TCR is selecting from the group consisting of a TCR on a T cell, a soluble TCR, an isolated TCR, and an immobilized TCR.
15. The method of any one of embodiments 7-14, further comprising comparing the detected binding of said peptide to said MHC molecule or said TCR with a reference.
16. The method of embodiment 15, further comprising selecting the detected binding of said peptide over the reference, for the purposes of identifying antigens in infection, autoimmunity, allergy, or cancer, or for vaccine design.
17. The method of any one of embodiments 7-16, wherein the polynucleotide and the probe are selected from the group consisting of DNA, cDNA, RNA, mRNA, rRNA, tRNA, PNA, a DNA-like molecule or an RNA-like molecule.
18. The method of any one of embodiments 7-17, wherein the binding of said probe to said polynucleotide is detected by gel electrophoresis, hybridization, PCR, qPCR, or nucleotide sequencing.
19. The method of any one of embodiments 7-18, wherein the MHC molecule is immobilized.
20. The method of any one of embodiments 7-19, wherein said polynucleotide-peptide conjugate is multimerized or oligomerized.
21. The method of any one of embodiments 7-20 performed in a high throughput fashion.
22. The method of any one of embodiments 7-20, which further comprises one or more of the steps of:
allowing binding between the polynucleotide-peptide conjugate and the MHC molecule to reach equilibrium; washing the complex between the polynucleotide-peptide conjugate and the MHC molecule under a suitable condition to remove unbound or non-specifically bound polynucleotide-peptide conjugate; allowing the complex between the polynucleotide-peptide conjugate and the MHC molecule to dissociate; and detecting the polynucleotide-peptide conjugate that remains bound to the MHC molecule.
23 The method of embodiment 22, wherein the complex between the polynucleotide-peptide conjugate and the MHC molecule is allowed to dissociate in the presence of one or more blocker species.
24. The method embodiment 23, wherein the one or more blocker species prevent binding or reassociation of the polynucleotide-peptide conjugate to the MHC molecule.
25. The method embodiment 23 or 24, wherein the blocker species compete with the polynucleotide-peptide conjugate for binding to the MHC molecule, and the binding between the blocker species and the MHC complex does not generate a signal indicative of specific binding between the polynucleotide-peptide conjugate and the MHC molecule.
26. The method of any one of embodiments 7-25, wherein the binding of the polynucleotide-peptide conjugate to the MHC molecule occurs in the presence of one or more chaperons.
27. The method of embodiment 26, wherein the chaperon is selected from the group consisting of a protein chaperon, a chemical chaperon, HLA-DM and an analogue thereof, a small molecule that has the same or similar chaperon function as HLA-DM, parachlorophenol (pCP) and an analogue thereof, and dimethylsulphoxide (DMSO) and an analogue thereof.

Example 1

Production of Peptide-cDNA Conjugates

Figure 9:
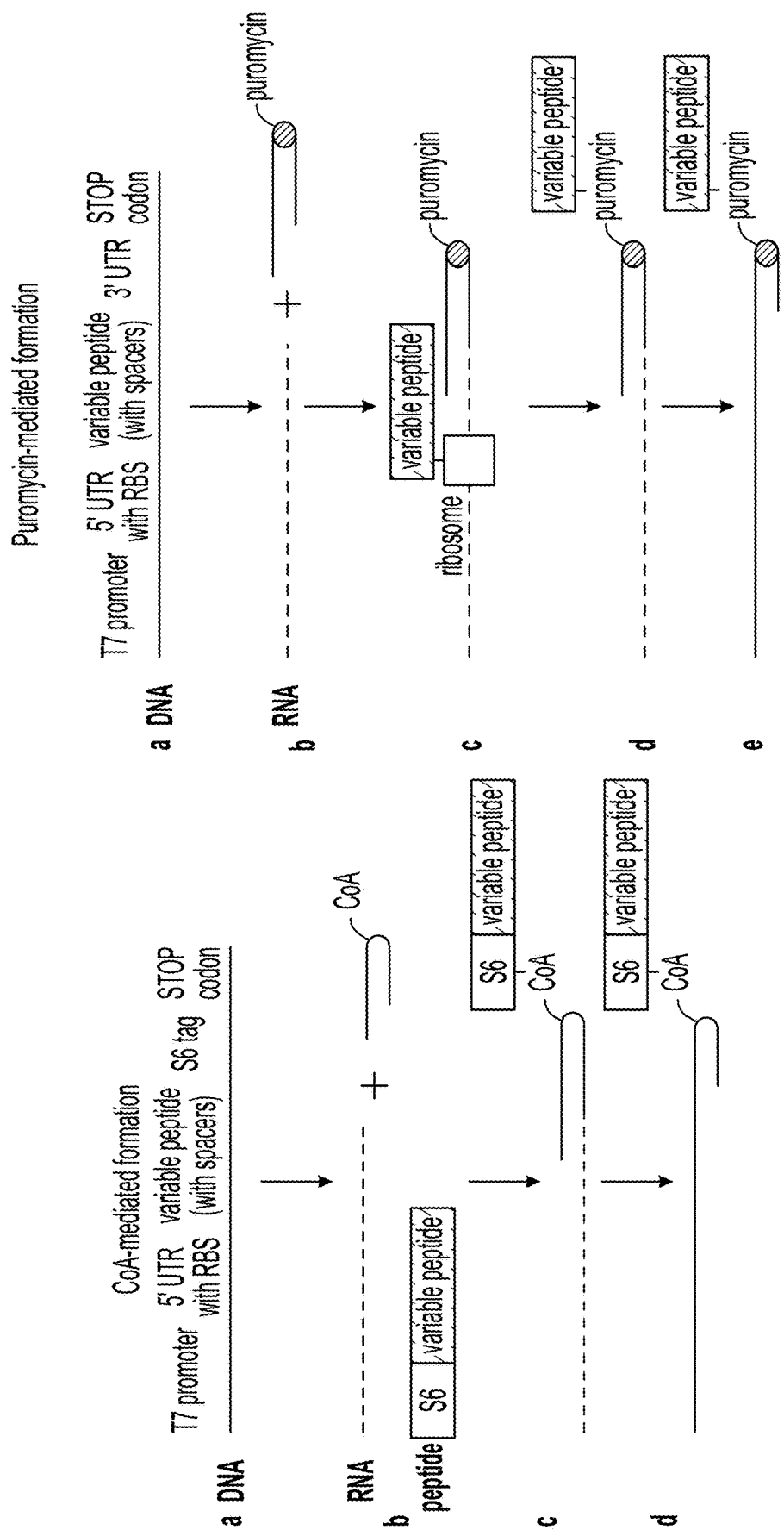
FIG. 9 shows representative methods for production of peptide-cDNA conjugates. In CoA-mediated formation, DNA templates (a) were transcribed and translated in the presence of a DNA adapter that includes a CoA moiety (b). Enzymatic attachment of adapter to RNA, and of peptide to adapter, resulted in the formation peptide-mRNA conjugates (c), that were then converted into a peptide-cDNA conjugates (d). In puromycin-mediated formation, DNA templates (a) were transcribed in vitro and ligated to puromycin-bearing DNA adapters (b). Upon in vitro translation of the purified transcript-adapter species (c), the ribosome mediated puromycin-peptide attachment to form peptide-mRNA conjugates (d), and these were then converted into peptide-cDNA conjugates (e).

Peptide-cDNA conjugates can be produced from DNA molecules by either CoA-mediated formation or puromycin-mediated formation. Each method can be implemented at high plexity, for example by using high-complexity microarrays as a source of DNA templates.
CoA-Mediated Formation
In this method, the reactions are conducted in one isolated compartment per sequence. As illustrated in FIG. 9 (left), peptide-cDNA conjugates are formed from DNA templates comprising the following elements (from 5' to 3'): (i) a T7 promoter, (ii) a 5' UTR sequence containing ribosomal binding site (RBS), (iii) a sequence encoding variable peptide (flanked by spacer residues), (iv) a sequence encoding S6 tag, and (v) a stop codon. In a single incubation mixture, these DNA templates are transcribed to form mRNAs, the mRNAs translated into peptides, and the mRNAs and peptides covalently attached to each other. Peptide-mRNA attachment occurs through a polyfunctional adapter molecule comprising a DNA hairpin (with an overhang region complementary to the conserved 3' end of the transcribed mRNAs) that is covalently attached, by means of a polyethylene glycol (PEG) linker moiety, to a coenzyme A (CoA) molecule. Attachment of mRNA to adapter is mediated by T4 DNA ligase, and attachment of peptide to adapter occurs by SFP synthase-mediated attachment of the CoA molecule to the S6 tag. Peptide-mRNA conjugates are then converted to peptide-cDNA conjugates using reverse transcriptase, followed by treatment with RNAse to degrade mRNA. Prepared peptide-cDNA conjugates are then isolated from the reaction mixture by capture onto beads bearing DNA baits complementary to a conserved DNA sequence present in all conjugates. As an optional further purification step, SFP synthase along with an excess of biotinylated S6 peptide, is added to bead-captured species. In this reaction, species containing unreacted CoA molecules are biotinylated and then depleted by means of streptavidin beads.
Puromycin-Mediated Formation
This method does not require that the reactions be conducted in one isolated compartment per sequence. As previously described (Kozlov et al., 2012, PLoS One 7:e37441) and illustrated in FIG. 9 (right), peptide-cDNA conjugates are formed from DNA templates comprising the following elements (from 5' to 3'): (i) a T7 promoter, (ii) a 5' UTR sequence containing ribosomal binding site, (iii) a sequence encoding variable peptide (flanked by spacer residues), (iv) a stop codon, and (v) a 3' UTR region. To form conjugates, DNA templates are transcribed to form mRNA. The mRNA is then purified and attached to a polyfunctional adapter molecule comprising a DNA molecule (with a region complementary to the conserved 3' end of the transcribed mRNAs) that is covalently attached, by means of a linker moiety, to a puromycin molecule. The resulting adapter-mRNA conjugates are purified and then translated to form peptide-mRNA conjugates. The ribosomes mediate attachment between the newly-formed peptides and the puromycin molecule of the associated adapter-mRNA conjugates. Peptide-mRNA conjugates formed in this way are then converted to peptide-cDNA conjugates by the addition of reverse transcriptase, followed by treatment with RNAse to degrade mRNA. Prepared peptide-cDNA conjugates are then isolated from the reaction mixture by capture onto beads bearing DNA baits that are complementary to a conserved DNA sequence present in all conjugates.

Example 2

Multimerization of Peptide-cDNA Conjugates

This example describes representative methods for multimerization of peptide-cDNA conjugates. The preparation schemes described in Example 1 can be modified to enable applications that require multivalent peptide-cDNA conjugate molecules. These approaches for multimerization of peptide-cDNA conjugates can also be implemented in conjunction with each other to enable even higher order multiplexing.

Multimerization Mediated by Multivalent Adapters

In this approach, the adapter molecule that mediates the connection between peptide and mRNA is modified to include multiple peptide capture molecules. For example, the capture molecule is CoA in the case of CoA-mediated formation, and the capture molecule is puromycin in the case of puromycin-mediated formation. Multiple peptides are attached to a single mRNA molecule during the peptide-cDNA synthesis process.

To form a bivalent adapter for CoA-mediated formation, a DNA hairpin comprising amino-modifications on two of the bases is used. These sites are reacted with NHS-ester groups on bifunctional PEG crosslinker molecules. The other functionality of the PEG crosslinker, maleimide, is attached to CoA by reacting with an excess of CoA trilithium salt. The resulting doubly-PEGylated, doubly-CoA-modified adapter is purified by gel electrophoresis, and used as the adapter in the peptide-cDNA synthesis protocol described in Example 1.

Multimerization by Hybridization

Figure 10:
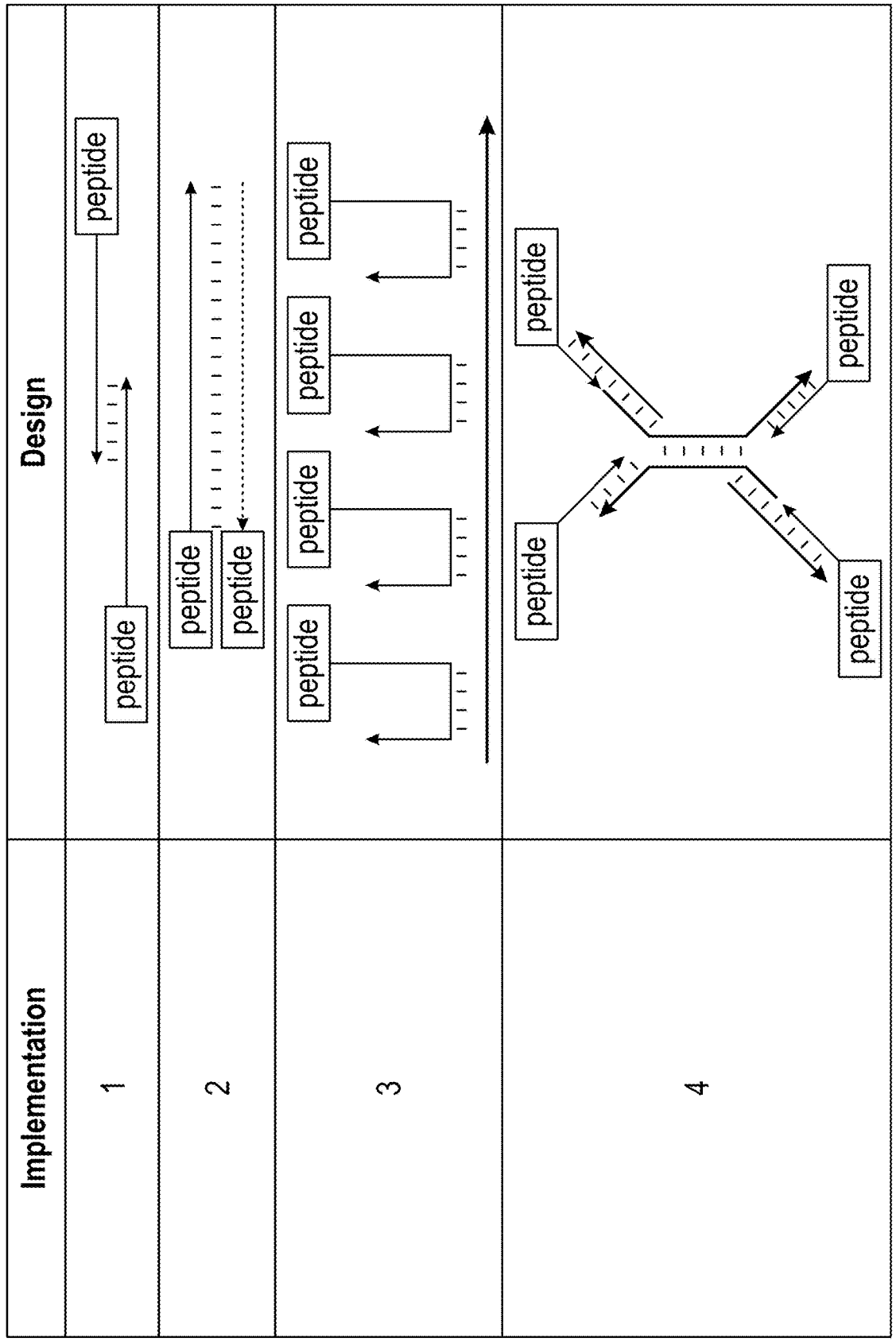
FIG. 10 shows multimerization of peptide-cDNA conjugates. Implementation 1 shows dimerization mediated by complementary sequence between two cDNA tags (solid lines). Implementation 2 shows dimerization mediated by intrinsic complementarity between mRNA tag (dashed line) and cDNA tag (solid line). Implementation 3 shows multimerization mediated by DNA linker (thicker solid line) containing repeats that are complementary to the cDNA tags. Implementation 4 shows multimerization mediated by hybridization-assembled DNA linker (thicker solid lines) containing regions that are complementary to the cDNA tags.

In this approach, peptide-cDNA conjugates are prepared in such a way that multiple conjugates can associate with each other by nucleic acid hybridization to form a multivalent conjugate. Various implementations are possible. In one implementation, DNA templates can be designed with complementary tag sequences so that they form hybrid pairs when mixed (implementation 1 of FIG. 10). In an alternative implementation, a fraction of the peptide-mRNA conjugate preparation can be retained and then mixed together with subsequently-formed peptide-cDNA conjugates (implementation 2 of FIG. 10). In alternative implementations, multimerization is mediated by separate linker DNA templates containing multiple complementary regions (implementations 3 and 4 of FIG. 10).

Example 3

Peptide-MHC Binding Assay

To test the binding of different peptides to MHC, peptide-cDNA conjugates were incubated overnight with biotinylated MHC molecules and then the MHC molecules were captured onto streptavidin-bearing beads. The beads were washed to remove unbound species, and then the remaining, MHC-bound peptide-cDNA conjugates were eluted under denaturing conditions and detected by gel electrophoresis, qPCR and/or DNA sequencing.

In the experiment shown in FIGS. 4A-4B, peptide-cDNA conjugates were produced by CoA-mediated formation as described in Example 1 with the following sequences: YKTIAFDEEARR (SEQ ID NO: 1) and YPKYVKQNTLKLAT (SEQ ID NO: 2). These sequences were derived from the proteomes of *Mycobacterium tuberculosis* and *Influenza A* virus, respectively. They were selected because they are known to bind respectively to the MHC class II molecules HLA-DR3 and HLA-DR1, without cross-binding (Sidney et al., 2002, J Immunol. 169: 5098-5108). Biotinylated HLA-DR3 and HLA-DR1 monomers were incubated overnight with the YKTIAFDEEARR (SEQ ID NO: 1 and YPKYVKQNTLKLAT (SEQ ID NO: 2) peptide-cDNA conjugates (as described in Sidney et al., 2001, Curr. Protoc. Immunol. Chapter 18: Unit 18.3), immobilized using streptavidin beads, washed 3 times with PBST, and the binding conjugates then eluted for analysis by gel electrophoresis and quantitative polymerase chain reaction. The results shown in FIGS. 4A-4B indicate that the eluted peptide-cDNA conjugates were detected by both readouts, and that each conjugate bound to the expected MHC molecule but not to the other HLA-DR family member.

In the experiment shown in FIG. 5, peptide-cDNA conjugates with the sequences YPKYVKQNTLKLAT ("YP (WT)") (SEQ ID NO: 3), YPKYVKQNTLKLAA ("YP (T14A)") (SEQ ID NO: 4), and YPKAVKQNTLKLAT ("YP (Y4A)") (SEQ ID NO: 5) were produced. Peptides of YP (WT), YP (T14A), and YP (Y4A) are known to bind the HLA-DR1 molecule with high, high, and low affinities, respectively. These three conjugates were then incubated, either individually (1-plex) or mixed together in equal quantities (3-plex), with biotinylated HLA-DR1 monomers and then eluted and analyzed by qPCR as described above. FIG. 5 shows that the expected profile of binding for the three conjugates (high, high, low) was detected, both in the case where conjugates were present individually (1-plex), and in the case where the conjugates were incubated and detected as a mixture (3-plex).

Example 4

Peptide:MHC-T Cell Binding Assay

To quantify different T cell specificities, multivalent peptide-cDNA conjugates can be incubated overnight with MHC molecules as in Example 3 above. The resulting incubation mixture contains multivalent peptide-cDNA conjugates where each peptide is bound to an MHC molecule "probe," unbound peptide-cDNA conjugates, and unbound MHC molecules. The resulting incubation mixture is then applied to a biological sample containing T cells. After a period of incubation, cells are pelleted and washed to remove species that do not bind to the T cells. Bound species are then eluted and detected by gel electrophoresis, qPCR and/or DNA sequencing.

Example 5

Peptide-MHC Binding Assay

Figure 6A:
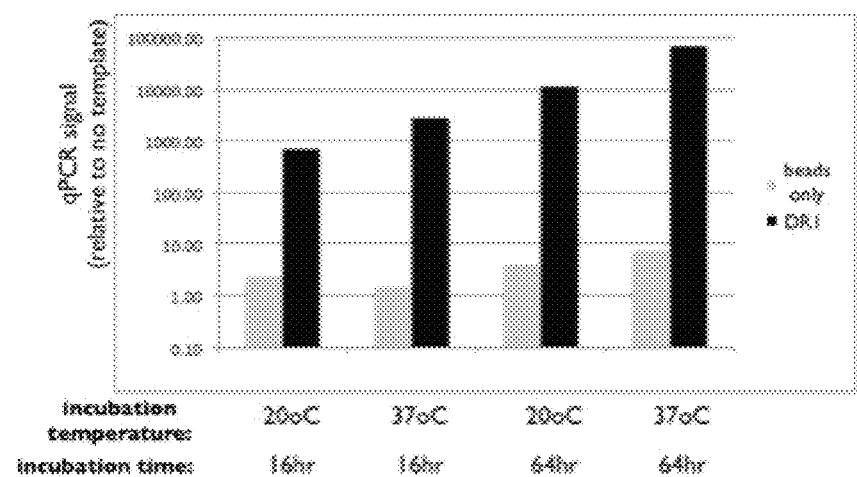
FIGS. 6A-6C show assay conditions for detection of specific peptide:MHC binding according to certain embodiments of the present disclosure.
Figure 6B:
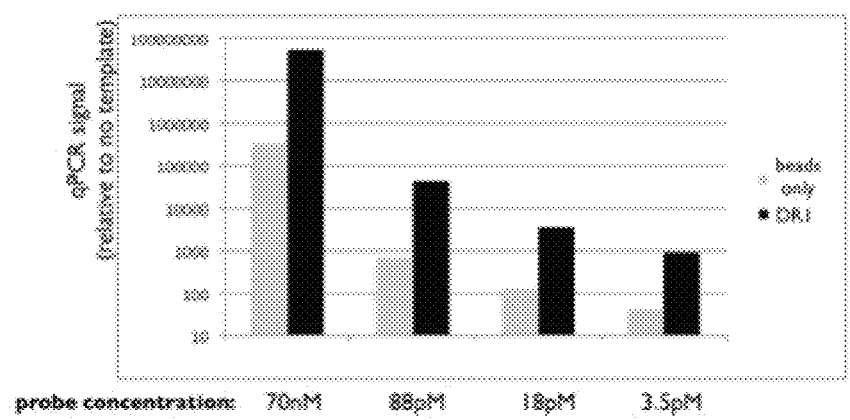

In this example, a 14-mer peptide (SEQ ID NO: 2, "YP") from the influenza virus, known to bind the MHA molecule HLA-DRB1*01:01, was chemically coupled to a 50-mer DNA oligonucleotide of a defined sequence. As shown in FIGS. 6A-6B, after purification, the resulting YP conjugate was incubated in the presence ("DR1") or absence ("beads only") of recombinant HLA-DRB1*01:01, then captured with beads bearing anti-HLA-DR antibody (L243), washed, eluted and then detected by qPCR reaction using primers specific for the attached DNA.

Figure 6C:
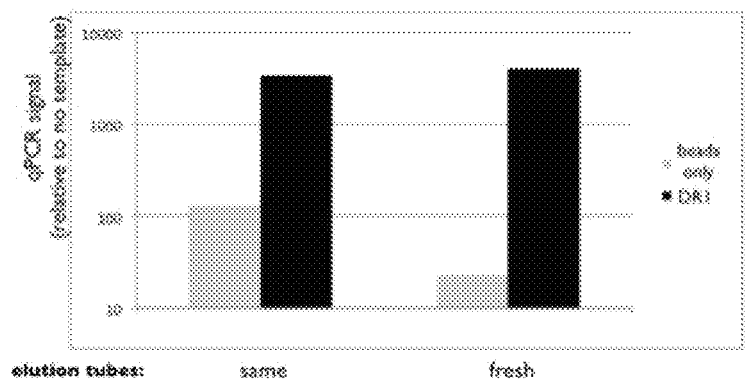

Shown in FIGS. 6A-6C are the qPCR results for 3 sequential experiments (i), (ii), and (iii). FIG. 6A shows qPCR results of experiment (i) under different incubation temperatures and times. FIG. 6B shows qPCR results of experiment (ii) using different concentrations of YP conjugate as input to the incubation. FIG. 6C shows qPCR results of experiment (iii) using fresh tubes for the elution.

Based on the results in experiment (i), the 37° C./16 hr incubation condition was fixed in experiments (ii) and (iii). Based on the results in experiment (ii), 18 pM was fixed in experiment (iii), being a concentration in the range of those achievable for a single species in a complex conjugate pool. Experiment (iii) shows that, under these conditions, a ~100-fold enrichment of YP conjugate binding to DR1 over beads is achieved when fresh elution tubes are used.

Example 6

Detection of Specific Peptide:MHC Binding Among a Pool of Polynucleotide-Peptide Conjugates A pool of 4000 custom-designed peptide-cDNA conjugates were designed using a publicly-available dataset of HLADRB1*01:01 binders (available at: http://bio.dfci.harvard.edu/DFRMLI/datasets/IEDB_DRB1_0101.htm) and synthesized using puromycin technology. Peptides "YP" (14-mer, SEQ ID NO: 2) and "YK" (12-mer, SEQ ID NO: 1) which are known to bind or not bind the MHA molecule HLA-DRB1*01:01, respectively, and each bearing a distinct 50-mer DNA oligonucleotide, were admixed to the ~4000-plex set at concentrations comparable to other members of the library, to generate a second pool. The resulting pools were applied in the assay as described in FIGS. 6A-6C, using either beads only or the HLA molecule DR1.

Figure 7A:
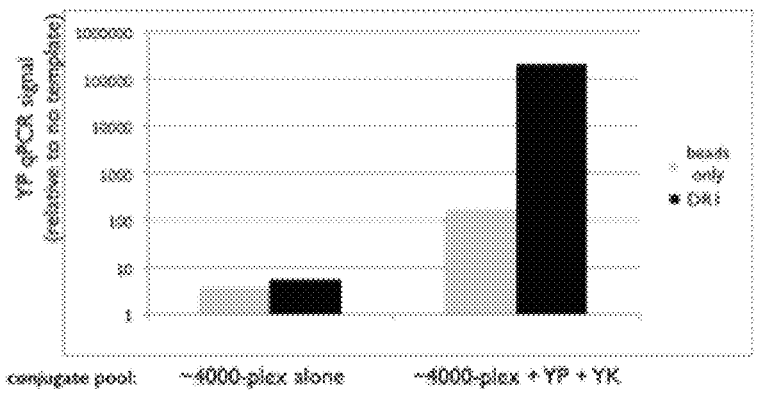
FIGS. 7A-7C show detection of specific peptide:MHC binding in a pool of polynucleotide-peptide conjugates, according to certain embodiments of the present disclosure.
Figure 7B:
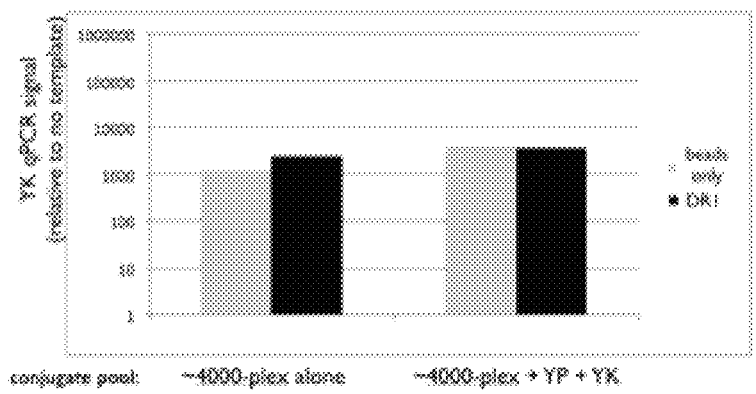
Figure 7C:
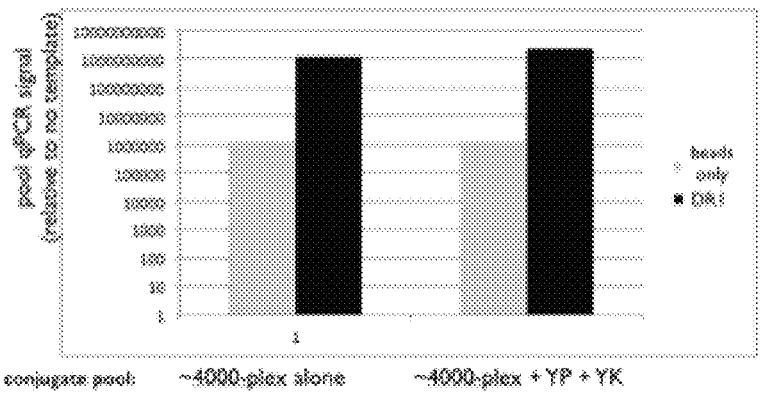

Shown are qPCR results for primer sets specific for YP (FIG. 7A), YK (FIG. 7B) and the puromycin pool (FIG. 7C). Whereas the specific conjugate (YP) is enriched ~1000-fold among the admixed pool in the DR1 condition compared to beads only (as shown in FIG. 7A), no such enrichment is observed for the non-DR1-specific conjugate (YK) (as shown in FIG. 7B). The pool itself was also enriched ~1000-fold in the DR1 condition compared to beads only (as shown in FIG. 7C).

Example 7

Detection of Specific Peptide:MHC Binding by Extension

Figure 8A:
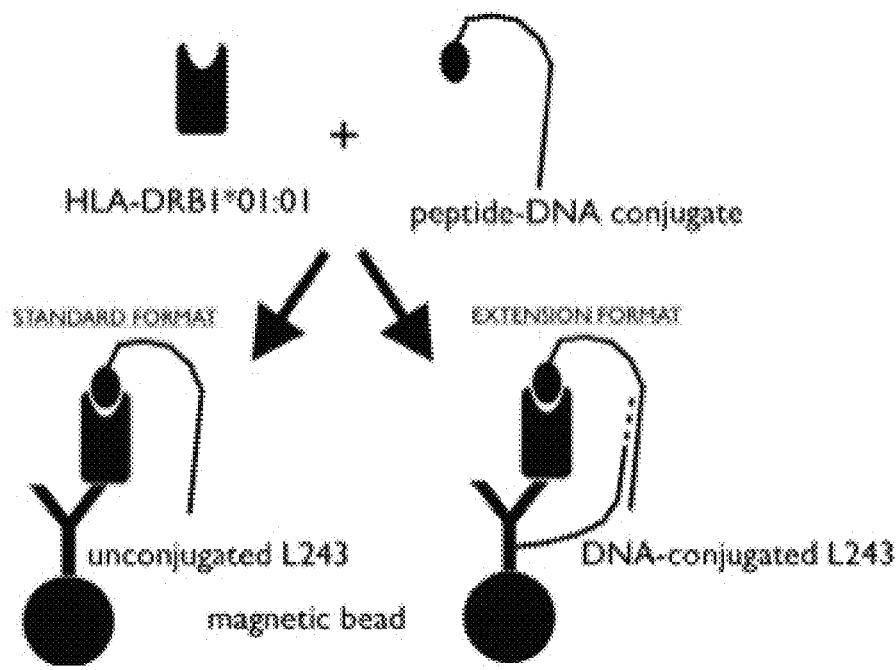
FIGS. 8A-8B show detection of specific peptide:MHC binding using the extension assay format, according to certain embodiments of the present disclosure.

A 12-mer peptide (SEQ ID NO: 1, "YK") from *M tuberculosis*, known to bind the MHA molecule HLA-DRB1*03:01, was chemically coupled to a 50-mer DNA oligonucleotide of a defined sequence. The MHC binding assay described in FIGS. 6A-6C was performed ("standard format"), or with the additional "extension assay format" depicted in FIG. 8A. In this extension format, the bead-bound anti-HLA-DR antibody ("L243") was conjugated to a ~40-mer DNA tag that included a 3' 7-mer sequence complementary to last 7 bases of the YK DNA tag. After washing, DNA polymerase was added to extend the tags, and product was detected using a qPCR primer set specific for the extension product.

Figure 8B:
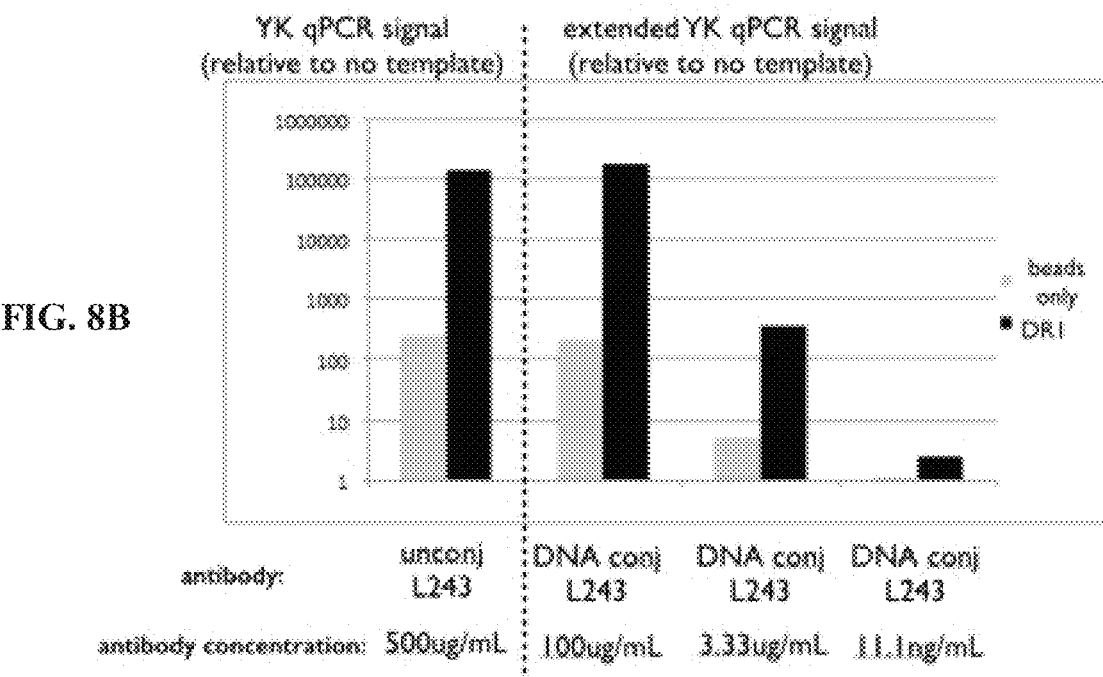

Shown in FIG. 8B are qPCR results for both the extension assay format and standard format, at the indicated concentrations of antibody. The results indicate that the extension assay format is capable of producing ~1000-fold enrichment of the YK signal in the DR1 condition compared to beads only.

All headings are for the convenience of the reader and should not be used to limit the meaning of the text that follows the heading, unless so specified.

Citation of the above publications or documents is not intended as an admission that any of them is pertinent prior art, nor does it constitute any admission as to the contents or date of these publications or documents.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

| Sequence Listing: | |
|---|---|
| SEQ ID NO | Sequence |
| 1 | YKTIAFDEEARR |
| 2 | YPKYVKQNTLKLAT |
| 3 | YPKYVKQNTLKLAT |
| 4 | YPKYVKQNTLKLAA |
| 5 | YPKAVKQNTLKLAT |
| 6 | PKYVKQNTLKLAT |
| 7 | QYIKANSKFIGITE |

The invention claimed is:

1. A composition comprising a plurality of complexes,
wherein each complex comprises a conjugate and a major histocompatibility complex (MHC) molecule, and the conjugate is a polynucleotide-candidate peptide conjugate,
wherein the polynucleotide of each conjugate is attached to the candidate peptide of the conjugate and uniquely identifies the candidate peptide,
wherein in each complex, the candidate peptide of the conjugate binds to the MHC molecule and is between 5 and 40 amino acid residues in length, inclusive, and
wherein the candidate peptides in the plurality of complexes form a library of candidates for binding to a T-cell receptor (TCR).

2. The composition of claim 1, wherein the polynucleotide of each conjugate comprises a primer binding site.

3. The composition of claim 1, wherein the polynucleotide of each conjugate comprises a DNA encoding the candidate peptide of the conjugate.

4. The composition of claim 1, wherein the polynucleotide of each conjugate comprises a cDNA.

5. The composition of claim 1, wherein the polynucleotide of each conjugate is covalently attached to the candidate peptide via a linker.

6. The composition of claim 1, wherein the candidate peptides are synthetically produced peptides.

7. The composition of claim 1, wherein the candidate peptides are randomly generated peptides.

8. The composition of claim 1, wherein the candidate peptides comprise at least one antigen selected from the group consisting of autoantigens, cancer antigens, infectious agents, toxins, and allergens.

9. The composition of claim 1, wherein the candidate peptides are between 9 and 11 amino acid residues in length, inclusive.

10. The composition of claim 1, wherein the candidate peptides are between 8 and 20 amino acid residues in length, inclusive.

11. The composition of claim 1, wherein the plurality of complexes comprise at least 100 different candidate peptides.

12. The composition of claim 1, wherein the plurality of complexes comprise at least 1,000 different candidate peptides.

13. The composition of claim 1, wherein the plurality of complexes comprise at least 10,000 different candidate peptides.

14. The composition of claim 1, wherein the plurality of complexes comprise at least 100,000 different candidate peptides.

15. The composition of claim 1, wherein the plurality of complexes are in a solution.

16. The composition of claim 1, wherein each conjugate comprises multiple molecules of the candidate peptide.

17. The composition of claim 16, wherein the multiple molecules of the candidate peptide are coupled to the polynucleotide via a multivalent adapter, wherein the multiple molecules of the candidate peptide are covalently linked to the polynucleotide, or wherein the multiple molecules of the candidate peptide are coupled by nucleic acid hybridization.

18. The composition of claim 1, further comprising the TCR.

19. The composition of claim 18, wherein the TCR is on a T cell, an isolated TCR, a soluble TCR, or an immobilized TCR.

* * * * *

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Peptide sequence in conjugate

<400> SEQUENCE: 1

Tyr Lys Thr Ile Ala Phe Asp Glu Glu Ala Arg Arg
1               5                   10
```

```
<210> SEQ ID NO 2
<211> LENGTH: 14
<212> TYPE: PRT
<213> ORGANISM: Artificial Sequence
<220> FEATURE:
<223> OTHER INFORMATION: Peptide sequence in conjugate

<400> SEQUENCE: 2

Tyr Pro Lys Tyr Val Lys Gln Asn Thr Leu Lys Leu Ala Thr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Peptide sequence in conjugate

<400> SEQUENCE: 3

Tyr Pro Lys Tyr Val Lys Gln Asn Thr Leu Lys Leu Ala Thr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide sequence in conjugate

<400> SEQUENCE: 4

Tyr Pro Lys Tyr Val Lys Gln Asn Thr Leu Lys Leu Ala Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Peptide sequence in conjugate

<400> SEQUENCE: 5

Tyr Pro Lys Ala Val Lys Gln Asn Thr Leu Lys Leu Ala Thr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Peptide sequence in conjugate

<400> SEQUENCE: 6

Pro Lys Tyr Val Lys Gln Asn Thr Leu Lys Leu Ala Thr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Peptide sequence in conjugate

<400> SEQUENCE: 7

Gln Tyr Ile Lys Ala Asn Ser Lys Phe Ile Gly Ile Thr Glu
1               5                   10
```